(12) United States Patent
Glombik et al.

(10) Patent No.: US 7,666,848 B2
(45) Date of Patent: *Feb. 23, 2010

(54) THIOPHENE GLYCOSIDE DERIVATIVES, PROCESSES FOR THE PREPARATION, MEDICAMENTS COMPRISING THESE COMPOUNDS, AND THE USE THEREOF

(75) Inventors: Heiner Glombik, Hofheim (DE); Wendelin Frick, Huenstetten-Beuerbach (DE); Hubert Heuer, Schwabenheim (DE); Werner Kramer, Mainz-Laubenheim (DE); Harm Brummerhop, Fankfurt (DE); Oliver Plettenburg, Hattersheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 101 days.

This patent is subject to a terminal disclaimer.

(21) Appl. No.: 11/464,338

(22) Filed: Aug. 14, 2006

(65) Prior Publication Data

US 2006/0293252 A1 Dec. 28, 2006

Related U.S. Application Data

(63) Continuation of application No. 10/616,945, filed on Jul. 11, 2003, now Pat. No. 7,101,856.

(60) Provisional application No. 60/425,684, filed on Nov. 12, 2002.

(30) Foreign Application Priority Data

Jul. 11, 2002 (DE) ................... 102 31 370

(51) Int. Cl.
A61K 31/70 (2006.01)
C07H 17/00 (2006.01)

(52) U.S. Cl. .............. 514/25; 536/4.1; 536/18.1; 536/18.4

(58) Field of Classification Search .......... None
See application file for complete search history.

(56) References Cited

U.S. PATENT DOCUMENTS

| 5,190,923 | A | 3/1993 | Vincent et al. |
| 6,221,633 | B1 | 4/2001 | Ertl et al. |
| 6,324,512 | B1 | 11/2001 | Junqua et al. |
| 6,380,230 | B1 | 4/2002 | Brodin et al. |

FOREIGN PATENT DOCUMENTS

| EP | 0 462 884 | 12/1991 |
| EP | 1 213 296 A1 | 6/2002 |
| EP | 1 277 736 | 1/2003 |
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 99/15525 | 4/1999 |
| WO | WO 00/40569 | 7/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 | 12/2000 |
| WO | WO 01/09111 | 2/2001 |
| WO | WO 01/83451 | 11/2001 |
| WO | WO 01/85695 | 11/2001 |
| WO | WO 01/91752 | 12/2001 |

OTHER PUBLICATIONS

J. Fuentes, et al., "Reactions of per-0-acetylglucosyl isothiocyanate with carbon bases. A new method for the stereocontrolled syntheses of nucleosides and glucosylaminothiophenes," Tetrahedron: Asymmetry, 9:2517-32 (1998).
H. Okada, et al., "Synthesis and antitumor activities of prodrugs of benzoylphenylureas," Chem. Pharm. Bull. 42(1) 57-61 (1994).
P. Tyle, "Iontophoretic Devices for Drug Delivery," Pharmaceutical Research, 3(6):318-26 (1986).
A. Asakawa, et al., "Cocaine-amphetamine-regulated transcript influences energy metabolism, anxiety and gastric emptying in mice," Horm Metab Res, 33:554-58 (2001).
D. W. Lee, et al., "Leptin agonists as a potential approach to the treatment of obesity," Drugs of the Future 26(9):873-81 (2001).
J. Salvador, et al., "Perspectives in the therapeutic use of leptin," Expert Opinion on Pharmacotherapy, 1615-22 (2001).
H. J. F. Zunft, et al., "Carob pulp preparation for treatment of hypercholesterolemia," Advances in Therapy, 8(5):230-36 (2001).
H. Fiesselmann, et al., Chem. Ber., 1907-13 (1956).
M. D. Mullican, et al., "Novel thiophene-, pyrrole-, furan-, and benzenecarboxamidotetrazoles as potential antiallergy agents," J. Med. Chem., 34:2186-94 (1991).
G. M. Karp, et al., "Preparation of 4-hydroxy-2-trifluoromethylthiophene: A novel bioisostere of α, α, α-trifluoro-m-cresol," Synthesis, 8:1078-80 (2000).
Derwent abstract for PCT application publication No. WO 01/83451.
Derwent abstract for PCT application publication No. WO 99/15525.
Derwent abstract for European application No. EP 0 462 884.
Fouda, Hassan G. et al., "Disposition and Metabolism of Tenidap in the Rat," Drug Metabolism and Disposition, 25(2):140-148 (1997).

*Primary Examiner*—Elli Peselev
(74) *Attorney, Agent, or Firm*—Barbara E. Kurys

(57) ABSTRACT

Novel thiophene glycoside derivatives of the formula I

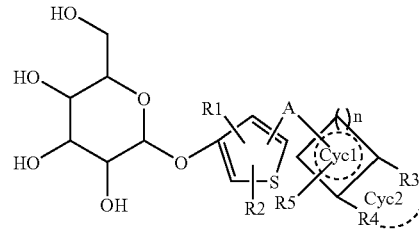

in which the radicals have the stated meanings, and the physiologically tolerated salts thereof and processes for their preparation are disclosed. The compounds are suitable, for example, as antidiabetics.

26 Claims, No Drawings

THIOPHENE GLYCOSIDE DERIVATIVES, PROCESSES FOR THE PREPARATION, MEDICAMENTS COMPRISING THESE COMPOUNDS, AND THE USE THEREOF

This application claims the benefit of priority under 35 U.S.C. 119(a) to German Application Number 10231370.9-43, filed on Jul. 11, 2002, which is hereby incorporated by reference. This case is a continuation of application Ser. No. 10/616,945, now U.S. Pat. No. 7,101,856.

The invention relates to substituted thiophene glycoside derivatives, to the physiologically tolerated salts thereof and to physiologically functional derivatives.

The antirheumatic tenidap (β-D-glucopyranoside uronic acid, 5-[(Z)-[1-(amino-carbonyl)-5-chloro-1,2-dihydro-2-oxo-3H-indol-3-ylidenehydroxymethyl-3-thienyl) (H. G. Fouda et al., CA: 1997;165448) is known, as are 3-amino-2-benzoyl-5-glucopyranosylaminothiophene compounds (J. Fuentes et al, Tetrahedron Asymmetry, 1998, 9, 2517-2532).

One embodiment of the invention is based on the object of providing novel compounds with which it is possible to prevent and treat type 1 and type 2 diabetes.

One embodiment of the invention, therefore, relates to compounds of the formula I

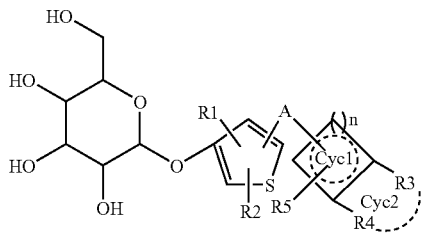

in which

R1, R2 are hydrogen, F, Cl, Br, I, OH, $NO_2$, CN, COOH, $CO(C_1-C_6)$-alkyl, $COO(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, $(C_1-C_6)$-alkoxy, $HO-(C_1-C_8)$-alkyl, $(C_1-C_6)$-alkoxy-$(C_1-C_6)$-alkyl, phenyl, benzyl, $(C_1-C_4)$-alkylcarbonyl, where one, more than one or all hydrogen(s) in the alkyl and alkoxy radicals may be replaced by flourine;
$SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_o$-phenyl, $SO-(C_1-C_6)$-alkyl, $SO-(CH_2)_o$-phenyl, $SO_2-(C_1-C_6)$-alkyl, $SO_2-(CH_2)_o$-phenyl, where o may be 0-6 and the phenyl radical may be substituted up to twice by F, Cl, Br, OH, $CF_3$, $NO_2$, CN, $OCF_3$, $(C_1-C_6)$-alkoxy, $(C_1-C_6)$-alkyl, $NH_2$;
$NH_2$, $NH-(C_1-C_6)$-alkyl, $N((C_1-C_6)$-alkyl$)_2$, $NH(C_1-C_7)$-acyl, phenyl, $O-(CH_2)_o$-phenyl, where o may be 0-6 and where the phenyl ring may be substituted one to 3 times by F, Cl, Br, I, OH, $CF_3$, $NO_2$, CN, $OCF_3$, $(C_1-C_6)$-alkoxy, $(C_1-C_6)$-alkyl, $NH_2$, $NH(C_1-C_6)$-alkyl, $N((C_1-C_6)$-alkyl$)_2$, $SO_2-CH_3$, COOH, COO-$(C_1-C_6)$-alkyl, $CONH_2$;
A is $(C_0-C_{15})$-alkanediyl, where one or more carbon atoms in the alkanediyl radical may be replaced independently of one another by $-O-$, $-(C=O)-$, $-CH=CH-$, $-C\equiv C-$, $-CH(OH)-$, $-CHF-$, $-CF_2-$, $-(S=O)-$, $-(SO_2)-$, $-N((C_1-C_6)$-alkyl$)-$, $-N((C_1-C_6)$-alkylphenyl$)-$ or $-NH-$;
n is a number from 0 to 4;

Cyc1 is a 3- to 7-membered, saturated, partially saturated or unsaturated ring, where 1 carbon atom may be replaced by O or S;
R3, R4, R5 are hydrogen F, Cl, Br, I, OH, $NO_2$, CN, COOH, $COO(C_1-C_6)$-alkyl, $CO(C_1-C_4)$-alkyl, $CONH_2$, $CONH(C_1-C_6)$-alkyl, $CON[(C_1-C_6)$-alkyl$]_2$, $(C_1-C_8)$-alkyl, $(C_2-C_6)$-alkenyl, $(C_2-C_6)$-alkynyl, $(C_1-C_{12})$-alkoxy, $HO-(C_1-C_6)$-alkyl, $(C_1-C_6)$-alkoxy-$(C_1-C_6)$-alkyl, where one, more than one or all hydrogen(s) in the alkyl and alkoxy radicals may be replaced by fluorine;
$SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_o$-phenyl, $SO-(C_1-C_6)$-alkyl, $SO-(CH_2)_o$-phenyl, $SO_2-(C_1-C_6)$-alkyl, $SO_2-(CH_2)_o$-phenyl, where o may be 0-6 and the phenyl radical may be substituted up to twice by F, Cl, Br, OH, $CF_3$, $NO_2$, CN, $OCF_3$, $(C_1-C_6)$-alkoxy, $(C_1-C_6)$-alkyl, $NH_2$;
$NH_2$, $NH-(C_1-C_6)$-alkyl, $N((C_1-C_6)$-alkyl$)_2$, $NH(C_1-C_7)$-acyl, phenyl, $(CH_2)_o$-phenyl, $O-(CH_2)_o$-phenyl, where o may be 0-6 and where the phenyl ring may be substituted one to 3 times by F, Cl, Br, I, OH, $CF_3$, $NO_2$, CN, $OCF_3$, $(C_1-C_8)$-alkoxy, $(C_1-C_6)$-alkyl, $NH_2$, $NH(C_1-C_6)$-alkyl, $N((C_1-C_6)$-alkyl$)_2$, $SO_2-CH_3$, COOH, COO-$(C_1-C_6)$-alkyl, $CONH_2$;
or
R3 and R4 together with the carbon atoms carrying them are a 5- to 7-membered, saturated, partially or completely unsaturated ring Cyc2 where 1 or 2 carbon atom(s) in the ring may also be replaced by N, O or S, and Cyc2 may optionally be substituted by $(C_1-C_6)$-alkyl, $(C_2-C_5)$-alkenyl, $(C_2-C_5)$-alkynyl, where in each case one $CH_2$ group may be replaced by O, or substituted by H, F, Cl, OH, $CF_3$, $NO_2$, CN, $COO(C_1-C_4)$-alkyl, $CONH_2$, $CONH(C_1-C_4)$-alkyl, $OCF_3$; and
R5 is hydrogen;
and the pharmaceutically acceptable salts thereof.

Examples of compounds of the invention include compounds of the formula I in which A is linked to the thienyl ring in position 2.

Another embodiment of the invention relates to compounds of formula I in which

R1, R2 are hydrogen, F, Cl, Br, I, OH, $NO_2$, CN, COOH, $CO(C_1-C_6)$-alkyl, $COO(C_1-C_6)$-alkyl, $CONH_2$, $CONH(C_1-C_6)$-alkyl, $CON[(C_1-C_6)$-alkyl$]_2$, $(C_1-C_8)$-alkyl, $(C_2-C_6)$-alkenyl, $(C_2-C_6)$-alkynl, $(C_1-C_6)$-alkoxy, $HO-(C_1-C_6)$-alkyl, $(C_1-C_6)$-alkoxy-$(C_1-C_6)$-alkyl, phenyl, benzyl, $(C_1-C_4)$-alkylcarbonyl, $SO-(C_1-C_6)$-alkyl, where one, more than one or all hydrogen(s) in the alkyl and alkoxy radicals may be replaced by fluorine;
A is $(C_0-C_{15})$-alkanediyl, where one or more carbon atom(s) in the alkanediyl radical may be replaced independently of one another by $-O-$, $-(C=O)-$, $-CH=CH-$, $-C\equiv C-$, $-S-$, $-CH(OH)-$, $-CHF-$, $-CF_2-$, $-(S=O)-$, $-(SO_2)-$, $-N((C_1-C_6)$-alkyl$)-$, $-N((C_1-C_6)$-alkylphenyl$)-$ or $-NH-$;
n is a number 2 or 3;
Cyc1 is a 5- to 6-membered, saturated, partially saturated or unsaturated ring, where 1 carbon atom may be replaced by O or S;
R3, R4, R5 are hydrogen, F, Cl, Br, I, OH, $NO_2$, CN, COOH, $COO(C_1-C_6)$-alkyl, $CO(C_1-C_4)$-alkyl, $CONH_2$, $CONH(C_1-C_6)$-alkyl, $CON[(C_1-C_6)$-alkyl$]_2$, $(C_1-C_8)$-alkyl, $(C_2-C_6)$-alkenyl, $(C_2-C_6)$-alkynyl, $(C_1-C_1)$-alkoxy, $HO-(C_1-C_6)$-alkyl, $(C_1-C_6)$-alkoxy-$(C_1-C_6)$-alkyl, $(C_1-C_4)$-alkylphenyl, $(C_1-C_4)$-alkoxyphenyl, $S-(C_1-C_6)$-alkyl, $SO-(C_1-C_6)$-alkyl, where one, more than one or all hydrogen(s) in the alkyl and alkoxy radicals may be replaced by fluorine;

or

R3 and R4 together with the carbon atoms carrying them are a 5- to 7-membered, saturated, partially, or completely unsaturated ring Cyc2, where 1 or 2 carbon atom(s) in the ring may also be replaced by N, O or S, and Cyc2 may optionally be substituted by $(C_1-C_6)$-alkyl, $(C_2-C_5)$-alkenyl, $(C_2-C_5)$-alkynyl, where in each case one $CH_2$ group may be replaced by O, or substituted by H, F, Cl, OH, $CF_3$, $NO_2$, CN, $COO(C_1-C_4)$-alkyl, $CONH_2$, $CONH(C_1-C_4)$-alkyl, $OCF_3$, and R5 is hydrogen.

Another embodiment of the invention relates to compounds of formula I in which

R1, R2 are hydrogen, $(C_1-C_6)$-alkyl, $(C_1-C_4)$-alkoxy, HO—$(C_1-C_4)$-alkyl, $(C_1-C_4)$-alkoxy-$(C_1-C_4)$-alkyl, F, Cl, $CF_3$, $OCF_3$, $OCH_2CF_3$ $(C_1-C_4)$-alkyl-$CF_2$—, phenyl, benzyl, $(C_1-C_4)$-alkylcarbonyl, $(C_2-C_4)$-alkenyl, $(C_2-C_4)$-alkynyl, $COO(C_1-C_4)$-alkyl;

A is —CH=CH—$CH_2$— or $(C_1-C_4)$-alkanediyl, where one or two $CH_2$ groups may also be replaced by —(C=O)—, —CH=CH—, —CH(OH)—, —NH—, —CHF—, —$CF_2$—, —O—;

n is a number 2 or 3;

Cyc1 is unsaturated ring, where 1 carbon atom may be replaced by O or S;

R3, R4, R5 are hydrogen, F, Cl, Br, I, $NO_2$, OH, CN, $(C_1-C_6)$-alkyl, $(C_1-C_8)$-alkoxy, $OCF_3$, $OCH_2CF_3$, S—$(C_1-C_4)$-alkyl, COOH, HO—$(C_1-C_4)$-alkyl, $(C_1-C_4)$-alkoxy-$(C_1-C_4)$-alkyl, $(C_1-C_2)$-alkylphenyl, $(C_1-C_2)$-alkoxyphenyl, or R3 and R4 together are —CH=CH—O—, —CH=CH—S—, —O—$(CH_2)_p$—O—, with p=1 or 2, —O—$CF_2$—O—, —CH=CH—CH=CH—, and R5 is hydrogen.

Examples of compounds of the invention include compounds of the formula I in which R2 is hydrogen.

Another embodiment of the invention relates to compounds of the formula I in which R1 is hydrogen, $CF_3$, $(C_1-C_4)$-alkyl, phenyl, R2 is hydrogen, A is —$CH_2$—, —$C_2H_4$—, —$C_3H_6$—, —CH(OH)—, —(C=O)—, —CH=CH—, —CH=CH—$CH_2$—, —CO—$CH_2$—$CH_2$— or —CO—NH—$CH_2$—;

n is a number 2 or 3;

Cyc1 is unsaturated ring, where 1 carbon atom may be replaced by S;

R3, R4, R5 are hydrogen, F, Cl, I, $NO_2$, OH, CN, $(C_1-C_6)$-alkyl, $(C_1-C_8)$-alkoxy, O—$CH_2$-Phenyl, $OCF_3$, S—$CH_3$, COOH or R3 and R4 together are —CH=CH—O—, —O—$(CH_2)_p$—O—, with p=1 or 2, —O—$CF_2$—O—, —CH=CH—CH=CH—, and R5 is hydrogen.

Another embodiment of the invention relates to compounds of the formula I in which A is —$CH_2$— or —$CH_2$—$CH_2$—, or Cyc1 is phenyl, or Cyc1 is thienyl.

Further examples of compounds of the invention include compounds of the formula I in which Cyc1 is monosubstituted, or Cyc1 is para-substituted, or Cyc1 is meta-substituted.

The invention also relates to compounds of the formula I in the form of their racemates, racemic mixtures and pure enantiomers, and to their diastereomers and mixtures thereof.

The alkyl radicals, including alkoxy, alkenyl and alkynyl, in the substituents R1, R2, R3, R4 and R5 may be either straight-chain or branched.

The sugar residues in the compounds of the formula I are either L- or D-sugars in their alpha ($\alpha$) and beta ($\beta$) form, such as, for example, allose, altrose, glucose, mannose, gulose, idose, galactose, talose. Examples of these sugars include: $\beta$-glucose, $\beta$-galactose, and $\alpha$-mannose; for instance $\beta$-glucose, $\beta$-allose and $\alpha$-mannose; for example $\beta$glucose.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the present specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from teh standard deviation found in their respective testing measurements.

Pharmaceutically acceptable salts are suitable for medical applications because of their greater solubility in water compared with the starting or base compounds. These salts have a pharmaceutically acceptable anion or cation. Suitable pharmaceutically acceptable acid addition salts of the compounds of the invention include salts of inorganic acids such as hydrochloric acid, hydrobromic, phosphoric, metaphosphoric, nitric and sulfuric acids, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acids. Suitable pharmaceutically acceptable basic salts include ammonium salts, alkali metal salts (such as sodium and potassium salts) and alkaline earth metal salts (such as magnesium and calcium salts), and salts of trometamol (2-amino-2-hydroxmethyl-1,3-propanediol), diethanolamine, lysine or ethylenediamine.

Salts with a pharmaceutically unacceptable anion such as, for example, trifluoroacetate, likewise belong within the scope of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester which is able, on administration to a mammal such as, for example, to a human, to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves have activity or not.

The compounds of the invention may also exist in various polymorphous forms, for example as amorphous and crystalline polymorphous forms. All polymorphous forms of the compounds of the invention belong within the scope of the invention and are a further aspect of the invention.

All references hereinafter to "compound(s) of formula I" refer to compound(s) of the formula I as described above, and to the salts, solvates and physiologically functional derivatives thereof as described herein.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 1.0 to 1000 mg, typically from 10 to 600 mg. An effective amount of a compound of the invention is an amount sufficient to bring about the recited effect. For the therapy of the abovementioned conditions, the compounds of formula I may be used as the compound itself, but they may be in the form of a pharmaceutical composition with an acceptable carrier. The carrier must, of course, be acceptable in the sense that it is compatible with the other ingredients of the composition and is not harmful for the patient's health. The carrier may be a solid or a liquid or both and may be formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention include those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention, as are acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, wafers, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet an be produced by compressing or molding a powder of granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound which is in powder form and is moistened with an inert liquid diluent in a suitable machine.

Pharmaceutical compositions that are suitable for peroral (sublingual) administration comprise suckable tablets, which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise, for example, sterile aqueous preparations of a compound of formula I, which may be isotonic with the blood of the intended recipient. These preparations are generally administered intravenously, although administration may also take place by subcutaneous, intramuscular or intradermal injection. These preparations can be produced, for example, by mixing the compound with water an making the resulting solution sterile and isotonic with blood. Injectable compositions of the invention generally contain from 0.1 to 5% by weight of the active compound.

Pharmaceutical compositions suitable for rectal administration may be in the form of single-dose suppositories. These can be produced by mixing a compound of the formula I with one or more conventional solid carriers, for example cocoa butter, and shaping the resulting mixture.

Pharmaceutical compositions suitable for topical use on the skin may be in the form of ointment, crème, lotion, paste, spray, aerosol or oil. Carriers that can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters, which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, for example about 3% to 15%. Another option is for the active ingredient to be released by electrotransport or iontophoresis as described, for example, in Pharmaceutical Research, 2(6): 318 (1986).

The invention further relates to processes for preparing the compounds of the formula I which can be obtained in accordance with teh following reaction schemes A, B, C, D and E:

Process A:

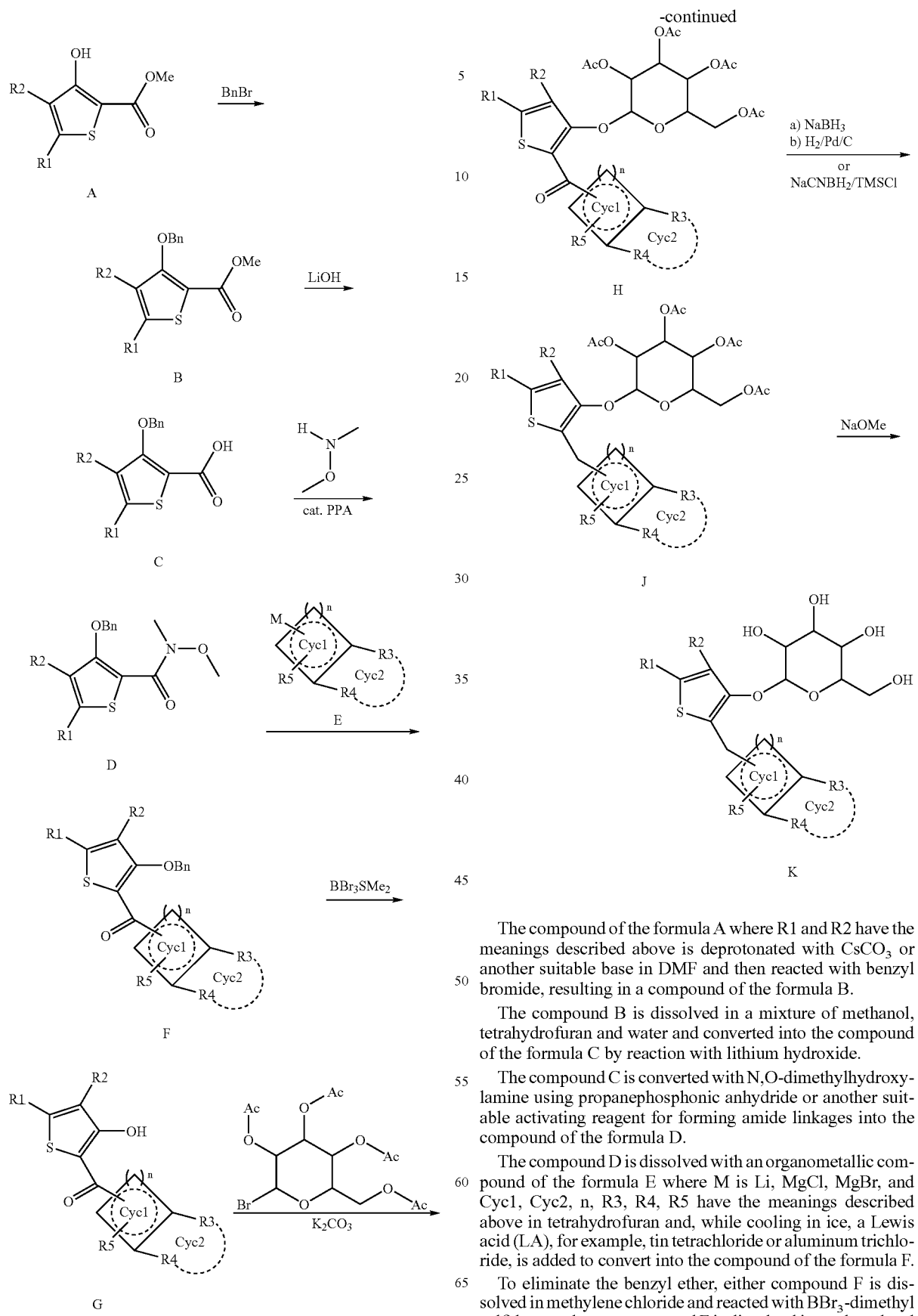

The compound of the formula A where R1 and R2 have the meanings described above is deprotonated with CsCO₃ or another suitable base in DMF and then reacted with benzyl bromide, resulting in a compound of the formula B.

The compound B is dissolved in a mixture of methanol, tetrahydrofuran and water and converted into the compound of the formula C by reaction with lithium hydroxide.

The compound C is converted with N,O-dimethylhydroxylamine using propanephosphonic anhydride or another suitable activating reagent for forming amide linkages into the compound of the formula D.

The compound D is dissolved with an organometallic compound of the formula E where M is Li, MgCl, MgBr, and Cyc1, Cyc2, n, R3, R4, R5 have the meanings described above in tetrahydrofuran and, while cooling in ice, a Lewis acid (LA), for example, tin tetrachloride or aluminum trichloride, is added to convert into the compound of the formula F.

To eliminate the benzyl ether, either compound F is dissolved in methylene chloride and reacted with BBr₃-dimethyl sulfide complex, or compound F is dissolved in methanol and stirred under a hydrogen atmosphere with palladium on carbon, and the compound of the formula G is obtained.

The compound G is converted with 4,5-diacetoxy-6-acetoxymethyl-2-bromo-tetrahydropyran-3-yl acetate and potassium carbonate in a mixture of methylene chloride and water into the compound of the formula H.

Either compound H is first reacted with sodium borohydride in a mixture of methanol and tetrahydorfuran and then converted in ethanol under a hydrogen atmosphere in the presence of palladium on carbon into the compound of the formula J, or compound H is dissolved in acetonitrile and converted directly to the compound of the formula J in a mixture of sodium cyanoborohydride and chlorotrimethylsilane.

The compound J is dissolved in methanol and reacted with sodium methanolate, resulting in the compound of the formula K.

The compounds of examples 51 to 54 are synthesized using this process.

Process B:

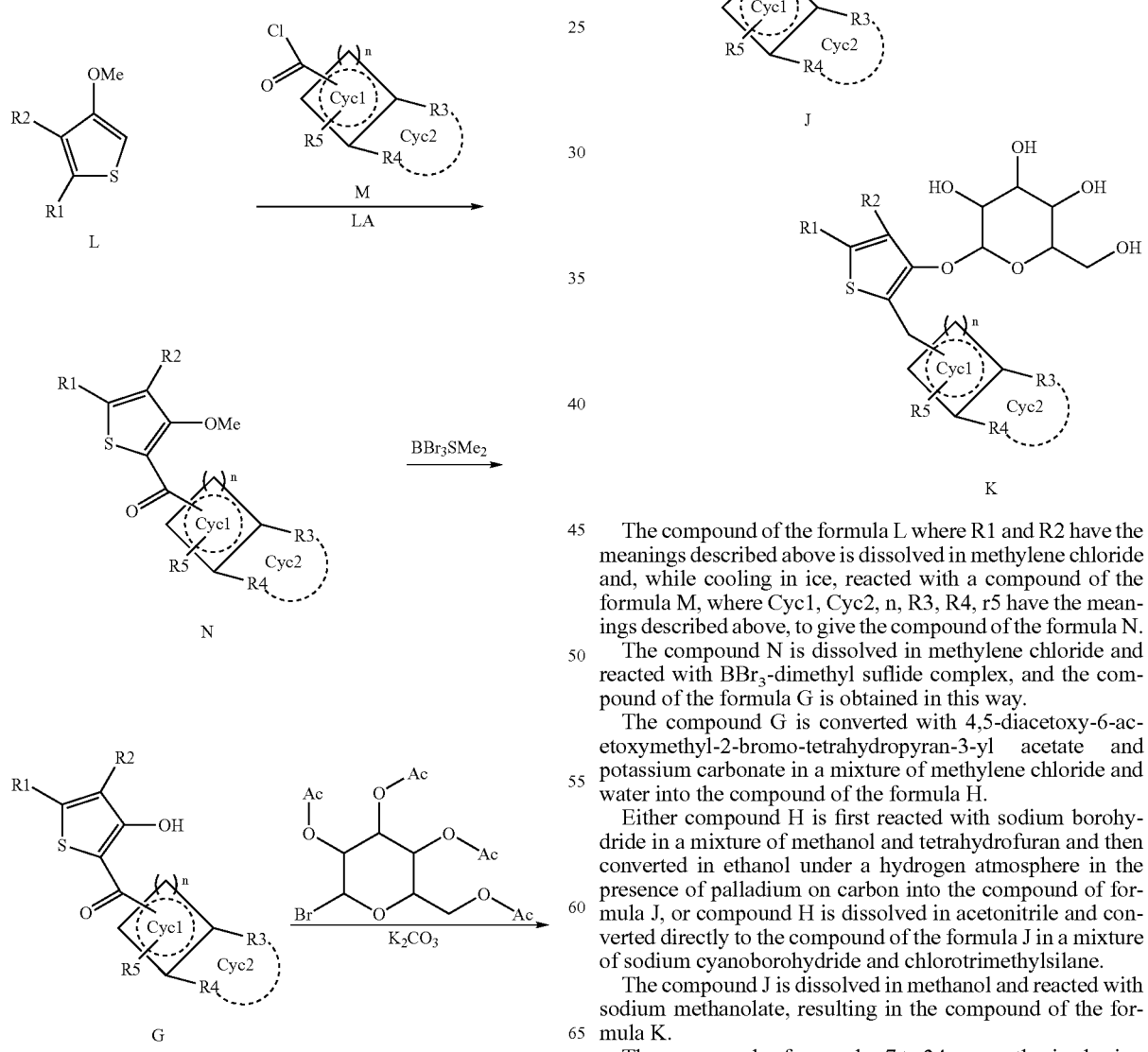

The compound of the formula L where R1 and R2 have the meanings described above is dissolved in methylene chloride and, while cooling in ice, reacted with a compound of the formula M, where Cyc1, Cyc2, n, R3, R4, r5 have the meanings described above, to give the compound of the formula N.

The compound N is dissolved in methylene chloride and reacted with BBr$_3$-dimethyl suflide complex, and the compound of the formula G is obtained in this way.

The compound G is converted with 4,5-diacetoxy-6-acetoxymethyl-2-bromo-tetrahydropyran-3-yl acetate and potassium carbonate in a mixture of methylene chloride and water into the compound of the formula H.

Either compound H is first reacted with sodium borohydride in a mixture of methanol and tetrahydrofuran and then converted in ethanol under a hydrogen atmosphere in the presence of palladium on carbon into the compound of formula J, or compound H is dissolved in acetonitrile and converted directly to the compound of the formula J in a mixture of sodium cyanoborohydride and chlorotrimethylsilane.

The compound J is dissolved in methanol and reacted with sodium methanolate, resulting in the compound of the formula K.

The compounds of examples 7 to 34 are synthesized using this process.

Process C:
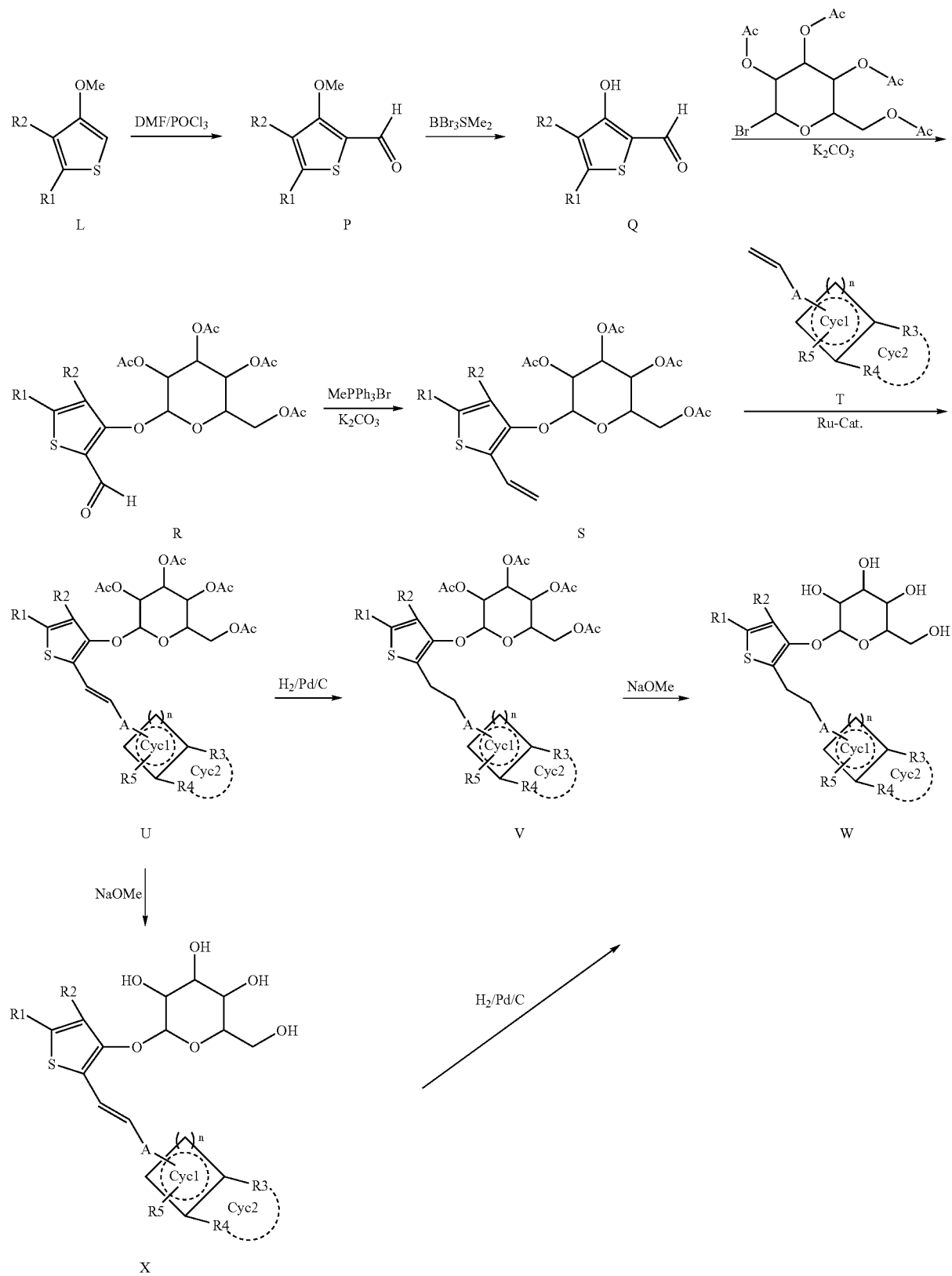

The compound of the formula L where R1 and R2 have the meanings described above is dissolved in DMF, and phosphoryl chloride is added, resulting in a compound of the formula P.

The compound P is dissolved in methylene chloride and reacted with BBr₃-demethyl sulfide complex, and the compound of the formula Q is obtained in this way.

The compound Q is converted with 4,5-diacetoxy-6-acetoxymethyl-2-bromo-tetrahydropyran-3-yl acetate and potassium carbonate in a mixture of methylene chloride and water into the compound of the formula R.

The compound R is dissolved in dioxane and converted with methyltriphenyl-phosphonium bromide and potassium carbonate into the compound of the formula S.

The compound S is converted in the presence of the ruthenium catalyst tricyclohexylphosphine-[1,3-bis(2,4,6-trimethylphenyl)-4,5-dihydroimidazol-2-ylidene][benzylidene] ruthenium(IV) dichoride in dichloromethan with the compound of the formula T, where A, Cyc1, Cyc2, n, R3, R4, R5 have the meanings described above, into the compound of the formula U.

The compound U is dissolved in methanol and reacted with sodium methanolate, resulting in the compound of the formula X.

Alternatively, the compound U can be converted in methanol under a hydrogen atmosphere in the presence of palladium on carbon into the compound of the formula V.

The compound V is dissolved in methanol and reacted with sodium methanolate, resulting in the compound of the formula W.

Alternatively, W can also be obtained by hydrogenolysis of X. This is done by treating X in methanol and in the presence of palladium on carbon under a hydrogen atmosphere.

The compounds of examples 36 to 50 are synthesized using this process.

Process D:

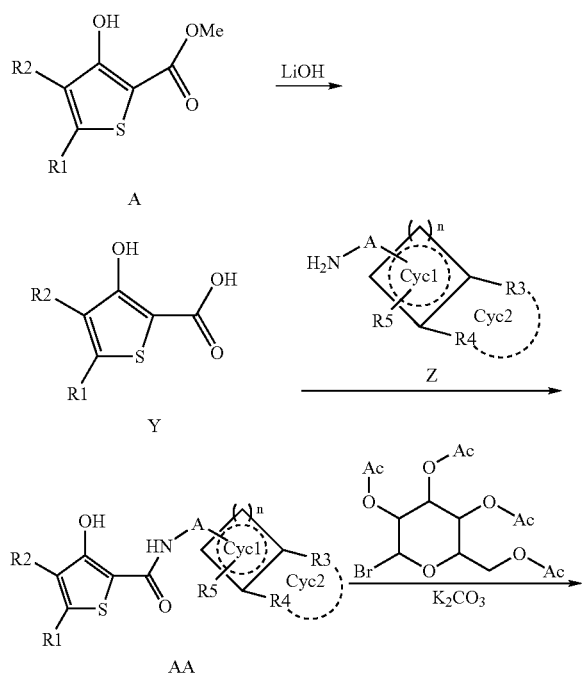

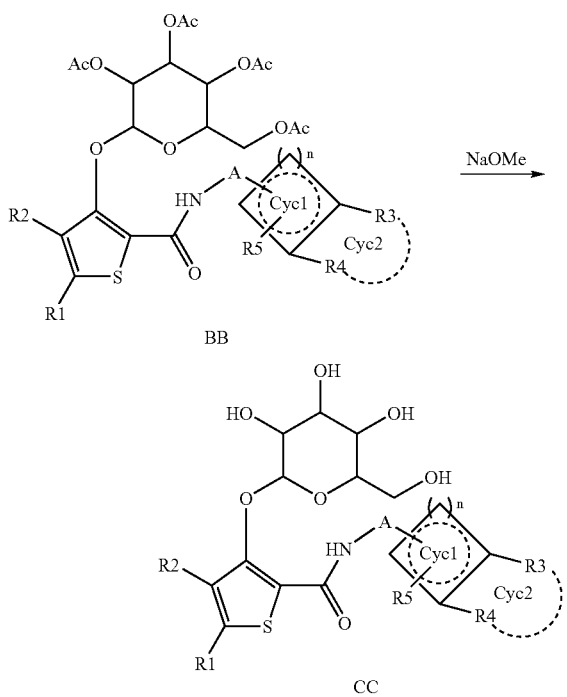

The compound of the formula A where R1 and R2 have the meanings described above is dissolved in a mixture of methanol, tetrahydrofuran and water and converted by reaction with lithium hydroxide into the compound of the formula Y.

The compound Y is dissolved with a compound of the formula Z where A, Cyc1, Cyc2, n, R3, R4, R5 have the meanings described above in tetrahydrofuran and, while cooling in ice, the compound is converted using propanephosphonic anhydride or another suitable activating reagent for forming amide linkages into the compound of the formula AA.

The compound AA is converted with 4,5-diacetoxy-6-acetoxymethyl-2-bromo-tetrahydropyran-3-yl acetate and potassium carbonate in a mixture of methylene chloride and water into the compound of the formula BB.

The compound BB is dissolved in methanol and reacted with sodium methanolate, resulting in the compound of the formula K.

The compounds of examples 55 to 58 were synthesized using this process.

Process E:

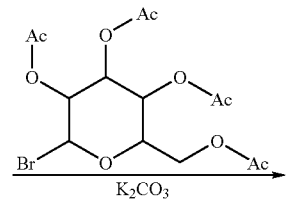

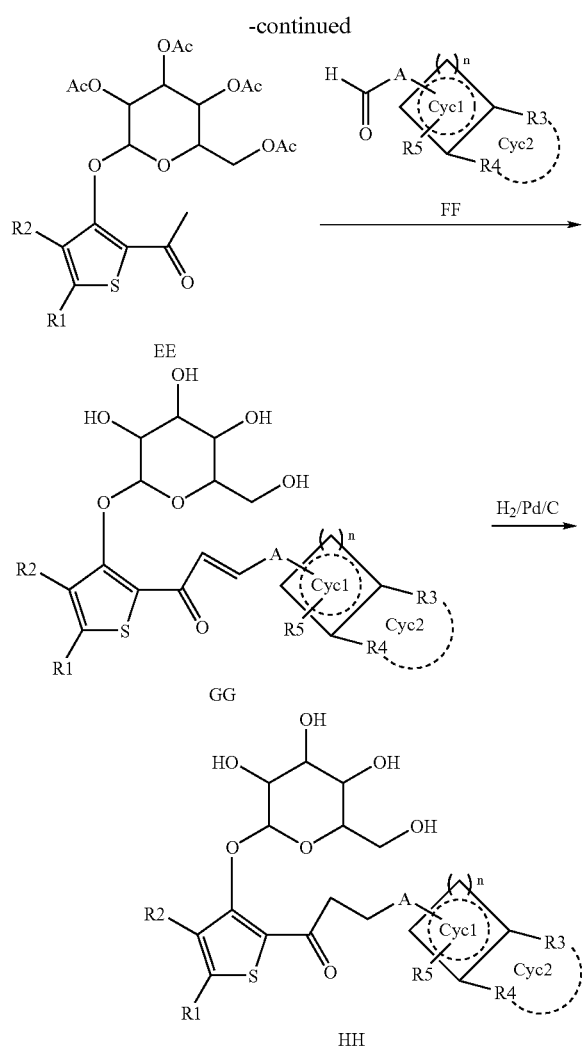

The compound DD is converted with 4,5-diacetoxy-6-acetoxymethyl-2-bromo-tetrahydropyran-3-yl acetate and potassium carbonate in a mixture of methylene chloride and water into the compound of the formula EE.

The compound EE is dissolved in methanol, and sodium methnaolate in methanol is added. A compound of the formula FF where A, Cyc1, Cyc2, n, R3, R4, R5 have the meanings described above is added, and a compound of the formula GG is obtained.

The compound GG is converted in methanol under a hydrogen atmosphere in the presence of palladium on carbon into the compound of formula HH.

The compounds of examples 1 to 6 are synthesized using this process.

Other compounds of the formula I can be prepared correspondingly or by analogy to known processes.

The compound(s) of the formula (I) can also be administered in combination with further active ingredients.

Further active ingredients suitable for combination products include:

all antidiabetics mentioned in chapter 12 of the Rote Liste 2001. They may be combined with the compounds of the formula I of the invention to achieve, for example a synergistic improvement. Administration of the active ingredient combination may take place either by separate administration of the active ingredients to the patients or in the form of combination products in which a plurality of active ingredients are present in one pharmaceutical preparation. Most of the active ingredients listed below are disclosed in USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 98/08871 of Novo Nordisk A/S, and orally active hypoglycemic active ingredients.

The orally active hypoglycemic active ingredients include, for example, sulfonylureas, biguanides, meglitinides, oxadiazolidinediones, thiazolidinediones, glucosidase inhibitors, glucagon antagonists, GLP-1 agonists, potassium channel openers such as, for example, those disclosed in WO 97/26265 WO 99/03861 of Novo Nordisk A/S, insulin sensitizers, inhibitors of liver enzymes involved in the stimulation of gluconeogenesis and/or glycogenolysis, modulators or glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMG-CoA reductase inhibitor such as simvastatin, fluvastatin, pravastatin, lovastatin, atorvastatin, cerivastatin, or rosuvastatin.

In one embodiment of the invention, the compounds of the formula I are administered in combination with a cholesterol absorption inhibitor such as, for example, ezetimibe, tiqueside, or pamaqueside.

In one embodiment of the invention, the compounds of the formula I are administered in combination with a PPAR gamma agonist such as, for example, rosiglitazone, pioglitazone, JTT-501, or GI 262570.

In one embodiment of the invention, the compounds of the formula I are administered in combination with PPAR alpha agonist such as, for example, GW 9578, or GW 7647.

In one embodiment of the invention, the compounds of the formula I are administered in combination with a mixed PPAR alpha/gamma agonist such as, for example, GW 1536, AVE 8042, AVE 8134, AVE 0847, or as described in WO 00/64888, WO 00/64876, or DE 10142734.4.

In one embodiment of the invention, the compounds of the formula I are administered in combination with a fibrate such as, for example, fenofibrate, clofibrate, or bezafibrate.

In one embodiment of the invention, the compounds of the formula I are administered in combination with an MTP inhibitor such as, for example, implitapide, BMS-201038, or R-103757.

In one embodiment of the invention, the compounds of the formula I are administered in combination with bile acid adsorption inhibitor (see e.g. U.S. Pat. No. 6,245,744 or U.S. Pat. No. 6,221,897), such as, for example, HMR 1741.

In one embodiment of the invention, the compounds of the formula I are administered in combination with a CETP inhibitor such as, for example, JTT-705.

In one embodiment of the invention, the compounds of the formula I are administered in combination with a polymeric bile acid adsorbent such as, for example, cholestyramine, or colesevelam.

In one embodiment of the invention, the compounds of the formula I are administered in combination with an LDL receptor inducer (see U.S. Pat. No. 6,324,512) such as, for example, HMR1171, or HMR1586.

In one embodiment of the invention, the compounds of the formula I are administered in combination with an ACAT inhibitor such as, for example, avasimibe.

In one embodiment of the invention, the compounds of the formula I are administered in combination with an antioxidant such as, for example, OPC-14117.

In one embodiment of the invention, the compounds of the formula I are administered in combination with a lipoprotein lipase inhibitor such as, for example, NO-1886.

In one embodiment of the invention, the compounds of the formula I are administered in combination with an ATP citrate lyase inhibitor such as, for example, SB-204990.

In one embodiment of the invention, the compounds of the formula I are administered in combination with a squalene synthetase inhibitor such as, for example, BMS-188494.

In one embodiment of the invention, the compounds of the formula I are administered in combination with a lipoprotein (a) antagonist such as, for example, CI-1027 or nicotinic acid.

In one embodiment of the invention, the compounds of the formula I are administered in combination with a lipase inhibitor such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide such as, for example, metformin.

In another embodiment, the compounds of the formula I are administered in combination with a meglitinide such as, for example, repaglinide.

In one embodiment, the compounds of the formula I are administered in combination with a thiazolidinedione such as, for example, troglitazone, ciglitazone, pioglitazone, rosiglitazone or the compounds disclosed in WO 97/41097 of Dr. Reddy's Research Foundation, for example 5-[[4-[(3,4-dihydro-3-methyl-4-oxo-2-quinazolinyl-methoxy]phenyl]methyl]-2,4-thiazolidinedione.

In one embodiment, the compounds of the formula I are administered in combination with an α-glucosidase inhibitor such as, for example, miglitol or acarbose.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.:Hormone and Metabolic Research (2001), 33(9), 554-558), NPY antagonists e.g. naphthalene-1-sulfonic acid {4-[(4-amino-quinazolin-2-ylamino)-methyl]-cyclohexylmethyl}-amide; hydrochloride (CGP 71683A)), MC4 agonists (e.g. 1-amino-1,2,3,4-tetrahydro-naphthalene-2-carboxylic acid [2-3a-benzyl-2-methyl-3-oxo-2,3,3a,4,6,7-hexahydro-pyrazolo[4,3-c]pyridin-5-yl)-1-(4-chloro-phenyl)-2-oxo-ethyl]-amide; (WO 01/91752)), orexin antagonists (e.g. 1-(2-methyl-benzoxazol-6-yl)-3-[1,5]naphthyridin-4-yl-urea; hydrochloride (SB-334867-A)), H3 agonists (3-cyclohexyl-1-(4,4-dimethyl-1,4,6,7-tetrahydro-imidazo[4,5-c]pyridin-5-yl)-propan-1-one oxalic acid salt (WO 00/063208)); TNF agonists, CRF antagonists (e.g. [2-methyl-9-(2,4,6-trimethyl-phenyl)-9H-1,3,9-triaza-fluoren-4-yl]-dipropyl-amine (WO 00/66585)), CRF BP antagonists (e.g. urocortin), urocortin agonists, β3 agonists (e.g. 1-(4-chloro-3-methanesulfonylmethyl-phenyl)-2-[2-(2,3-dimethyl-1H-indol-6-yloxy)-ethylamino]-ethanol; hydrochloride (WO 01/83451)), MSH (melanocyte-stimulating hormone) agonists, CCK-A agonists (e.g. {2-[4-(4-chloro-2,5-dimethoxy-phenyl)-5-(2-cyclohexyl-ethyl)-thiazol-2-yl-carbamoyl]-5,7-dimethyl-indol-1-yl}-acetic acid trifluoroacetic acid salt (WO 99/15525)); serotonin-reuptake inhibitors (e.g. dexfenfluramine, mixed serotoninergic and noradrenergic compounds (e.g. WO 00/71549), 5HT agonists e.g. 1-(3-ethyl-benzofuran-7-yl)-piperazine oxalic acid salt (WO 01/09111), bombesin agonists, galanin antagonists, growth hormone (e.g. human growth hormone), growth hormone-releasing compounds (6-benzyloxy-1-(2-diisopropylamino-ethylcarbamoyl)-3,4-dihydro-1H-isoquinoline-2-carboxylic acid tert-butyl ester (WO 01/85695)), TRH agonists (see e.g. EP 0 462 884), uncoupling protein 2 or 3 modulators, leptin agonists (see e.g. Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see e.g. "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphetamine or amphetamine.

In one embodiment, the other active ingredient is fenfluramine or dexfenfluramine.

In a further embodiment, the other active ingredient is sibutramine.

In one embodiment, the other active ingredient is orlistat.

In one embodiment, the other active ingredient is mazindol or phentermine.

In one embodiment, the compounds of the formula I are administered in combination with dietary fiber materials, for example, insoluble dietary fiber materials (see e.g. Carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax® Caromax® can moreover be administered in the form of foodstuffs such as, for example, in bakery products or muesli bars.

It is self-evident that any suitable combination of the compounds of the invention with one or more of the aforementioned compounds and optionally one or more other pharmacologically active substances is regarded as falling within the protection conferred by the present invention.

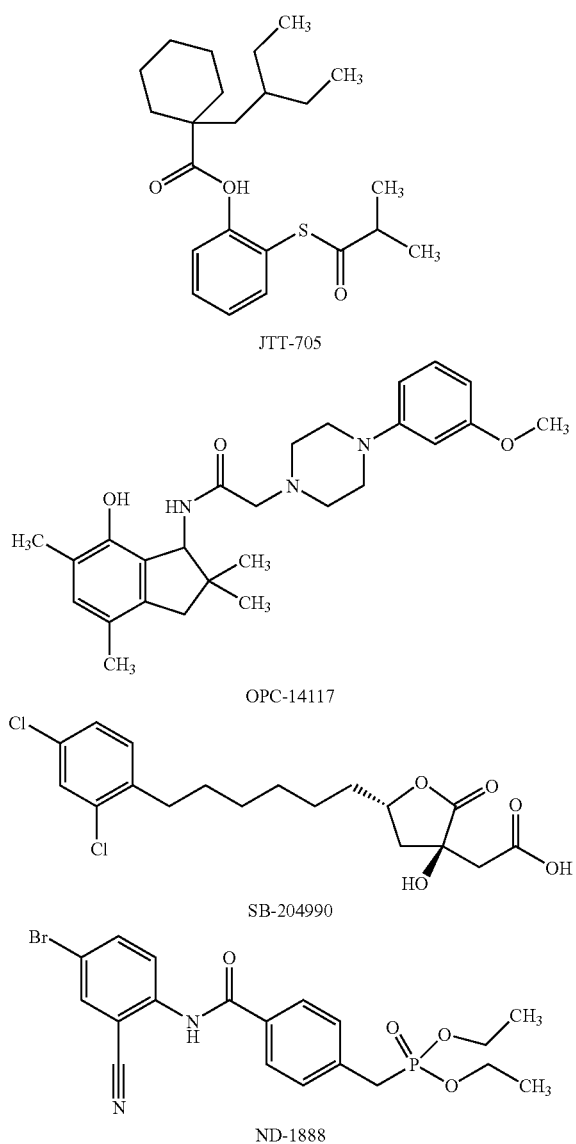
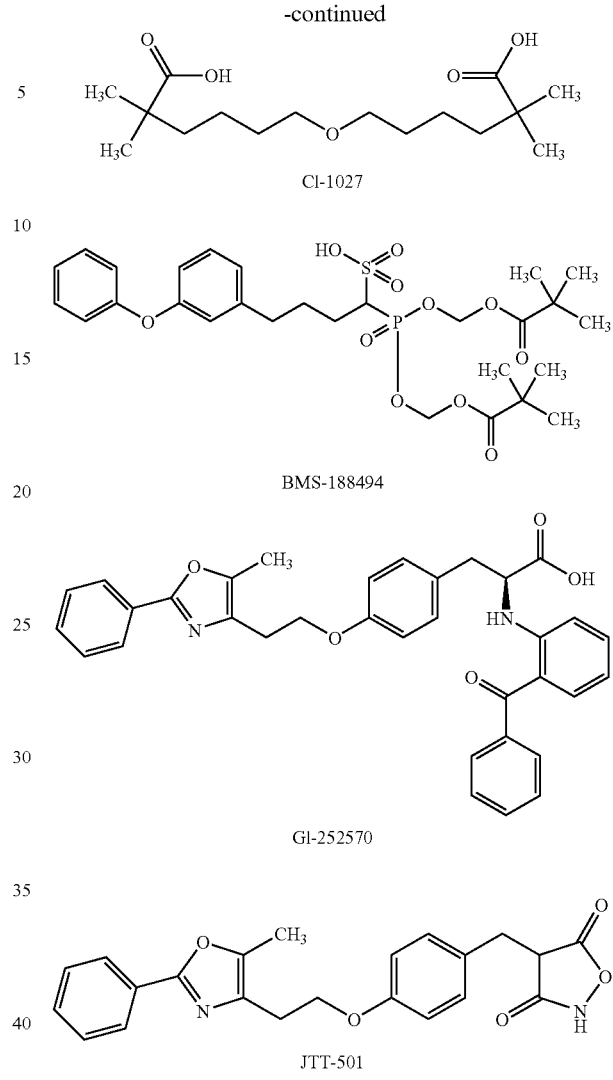
The examples detailed below serve to illustrate the invention without, however, restricting it.
TABLE 1
Compounds of the formula I
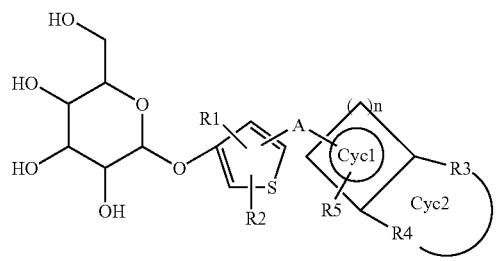
| Ex. | R1, R2 | A (linkage in thienyl 2 position) | Cyc1 | R3, R4, R5 | MS* |
|---|---|---|---|---|---|
| 1 | H, H | —CO—CH$_2$—CH$_2$— | Ph | 4-O—CH$_3$, H, H | ok |
| 2 | H, H | —CO—CH$_2$—CH$_2$— | Ph | 3-O—(CH$_2$)$_2$—O-4, H | ok |
| 3 | H, H | —CO—CH$_2$—CH$_2$— | Ph | 3-O—CH$_2$—O-4, H | ok |

TABLE 1-continued

Compounds of the formula I

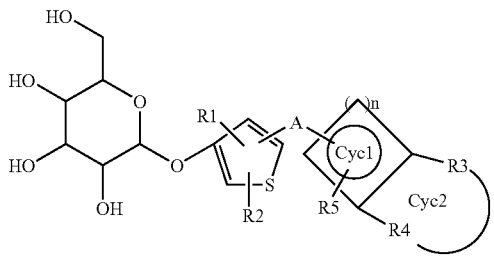

| Ex. | R1, R2 | A (linkage in thienyl 2 position) | Cyc1 | R3, R4, R5 | MS* |
|---|---|---|---|---|---|
| 4 | H, H | —CO—CH$_2$—CH$_2$— | Ph | 3-CH=CH—O-4, H | ok |
| 5 | H, H | —CO—CH$_2$—CH$_2$— | 3-thiophene | H, H, H | ok |
| 6 | H, H | —CO—CH$_2$—CH$_2$— | 2-thiophene | H, H, H | ok |
| 7 | H, H | —CH$_2$— | Ph | 4-O—CH$_3$, H, H | ok |
| 8 | H, H | —CO— | Ph | 4-O—CH$_3$, H, H | ok |
| 9 | H, H | —CH$_2$— | Ph | H, H, H | ok |
| 10 | H, H | —CH(OH)— | Ph | H, H, H | ok |
| 11 | H, H | —CH$_2$— | Ph | 4-O—C$_2$H$_5$, H, H | ok |
| 12 | H, H | —CH$_2$— | Ph | 3-O—CH$_3$, 4-O—CH$_3$, H | ok |
| 13 | H, H | —CH$_2$— | Ph | 4-O—C$_7$H$_{10}$, H, H | ok |
| 14 | H, H | —CH$_2$— | Ph | 4-F, H, H | ok |
| 15 | H, H | —CH$_2$— | Ph | 4-I, H, H | ok |
| 16 | H, H | —CH$_2$— | Ph | 4-NO$_2$, H, H | ok |
| 17 | H, H | —CH$_2$— | Ph | 4-CH$_3$, H, H | ok |
| 18 | H, H | —CH$_2$— | Ph | 3-CH$_3$, H, H | ok |
| 19 | H, H | —CH$_2$— | Ph | 2-CH$_3$, H, H | ok |
| 20 | H, H | —CH$_2$— | Ph | 4-C$_2$H$_5$, H, H | ok |
| 21 | H, H | —CH$_2$— | Ph | 3-CH$_3$, 4-O—CH$_3$, 5-CH$_3$ | ok |
| 22 | H, H | —CH$_2$— | Ph | 3-O—CF$_2$—O-4, H | ok |
| 23 | H, H | —CH$_2$— | Ph | 4-C$_3$H$_7$, H, H | ok |
| 24 | H, H | —CH$_2$— | Ph | 4-C(CH$_3$)$_3$, H, H | ok |
| 25 | H, H | —CH$_2$— | Ph | 4-OH, H, H | ok |
| 26 | H, H | —CH$_2$— | Ph | 4-O—CH$_2$—Ph, H, H | ok |
| 27 | H, H | —CH$_2$— | 3-thiophene | H, H, H | ok |
| 28 | H, H | —CH$_2$— | 2-thiophene | 4-CH=CH—CH=CH-5, H | ok |
| 29 | H, H | —CH$_2$— | Ph | 3-O—CH$_3$, H, H | ok |
| 30 | H, H | —CH$_2$— | Ph | 4-CN, H, H | ok |
| 31 | H, H | —CH$_2$— | Ph | 3-O—CH$_2$—O-4, H, H | ok |
| 32 | H, H | —CH$_2$— | Ph | 4-S—CH$_3$, H, H | ok |
| 33 | H, H | —CH$_2$— | Ph | 4-O—C$_4$H$_9$, H, H | ok |
| 34 | H, H | —CH$_2$— | Ph | 4-OCF$_3$, H, H | ok |
| 35 | H, H | —CH$_2$— | Ph | 4-COOH, H, H | ok |
| 36 | H, H | —CH$_2$—CH$_2$— | Ph | 4-O—CH$_3$, H, H | ok |
| 37 | H, H | —CH=CH— | Ph | 4-O—CH$_3$, H, H | ok |
| 38 | H, H | —CH=CH— | Ph | 4-F, H, H | ok |
| 39 | H, H | —CH=CH— | Ph | 4-Cl, H, H | ok |
| 40 | H, H | —CH=CH— | Ph | 4-O—C$_2$H$_5$, H, H | ok |
| 41 | H, H | —CH=CH— | Ph | 4-CH$_3$, H, H | ok |
| 42 | H, H | —CH=CH— | Ph | 4-OH, H, H | ok |
| 43 | H, H | —CH$_2$—CH$_2$— | Ph | 4-F, H, H | ok |
| 44 | H, H | —CH$_2$—CH$_2$— | Ph | 4-Cl, H, H | ok |
| 45 | H, H | —CH$_2$—CH$_2$— | Ph | 4-O—C$_2$H$_5$, H, H | ok |
| 46 | H, H | —CH$_2$—CH$_2$— | Ph | 4-CH$_3$, H, H | ok |
| 47 | H, H | —CH$_2$—CH$_2$— | Ph | 4-OH, H, H | ok |
| 48 | H, H | —CH=CH—CH$_2$— | Ph | 4-O—CH$_3$, H, H | ok |
| 49 | H, H | —CH$_2$—CH$_2$—CH$_2$— | Ph | 4-O—CH$_3$, H, H | ok |
| 50 | H, H | —CH=CH—CH$_2$— | Ph | 3-O—CH$_2$—O-4, H | ok |
| 51 | 5-CH(CH$_3$)$_2$, H | —CH$_2$— | Ph | 4-O—CH$_3$, H, H | ok |
| 52 | 5-Ph, H | —CH$_2$— | Ph | 4-O—CH$_3$, H, H | ok |
| 53 | 5-CH$_3$, H | —CH$_2$— | Ph | 4-O—CH$_3$, H, H | ok |
| 54 | 5-CF$_3$, H | —CH$_2$— | Ph | 4-O—CH$_3$, H, H | ok |
| 55 | H, H | —CO—NH—CH$_2$— | Ph | H, H, H | ok |
| 56 | H, H | —CO—NH—CH$_2$— | Ph | 4-O—CH$_3$, H, H | ok |
| 57 | H, H | —CO—NH—CH$_2$— | Ph | 3-O—CH$_2$—O-4, H | ok |
| 58 | H, H | —CO—NH—CH$_2$— | Ph | 4-O—CF$_3$, H, H | ok |

*The indication "MS is ok" means that a mass spectrum or HPLC/MS was recorded and the molecular peak M + 1 (MH$^+$) and/or M + 18 (MNH$_4^+$) and/or M + 23 (MNa$^+$) was detected therein The compounds of the formula I are distinguished by beneficial effects on glucose metabolism; for example, they lower the blood glucose level and are suitable for the treatment of type 1 and type 2 diabetes. The compounds can therefore be employed alone or in combination with other blood glucose-lowering active ingredients (antidiabetics).

The compounds of the formula I are further suitable for the prevention and treatment of late damage from diabetes, such as, for example, nephropathy, retinopathy, neuropathy and syndrome X, obesity, myocardial infarct, peripheral arterial occlusive diseases, thromboses, arteriosclerosis, inflammations, immune diseases autoimmune diseases such as, for example, AIDS, asthma, osteoporosis, cancer, psoriasis, Alzheimer's, schizophrenia and infectious diseases, treatment of type 1 and type 2 diabetes and the prevention and treatment of late damage from diabetes, syndrome X and obesity.

As used herein, treating or treatment includes the treating of, for example, a patient inflicted with a disease or condition, as well as the prevention, prophylaxis, or protective treatment of a patient. Treatment also includes treating a subject susceptible to or predisposed to developing a disease or condition, which could include patients in whom the disease or condition has not yet presented, as well as patients in whom the disease has been successfully treated but could redevelop or reoccur.

The activity of the compounds was tested as follows:

Preparation of Brush Border Membrane Vesicles from the Small Intestine of Rabbits, Rats and Pigs Preparation of brush border membrane vesicles from the intestinal cells of the small intestine was carried out by the so-called $Mg^{2+}$ precipitation method. The mucosa of the small intestine was scraped off and suspended in 60 of ice-cold Tris/HCl buffer (ph 7.1)/300 mM mannitol, 5 mM EGTA. Dilution to 300 ml with ice-cold distilled water was followed by homogenization with an Ultraturrax (18 shaft, IKA Werk Staufen, FRG) at 75% of the max. power for 2×1 minute, while cooling in ice. After addition of 3 ml of 1 M $MgCl_2$ solution (final concentration 10 mM), the mixture was left to stand at 0° C. for exactly 15 minutes. Addition of $Mg^{2+}$ causes the cell membranes to aggregate and precipitate with the exception of the brush border membranes. After centrifugation at 3 000×g (5 000 rpm, SS-34 rotor) for 15 minutes, the precipitate was discarded and the supernatant, which contained the brush border membranes, was centrifuged at 26 700×g (15 000 rpm, SS-34 rotor) for 30 minutes. The supernatant was discarded, and the precipitate was rehomogenized in 60 ml of 12 mM Tris/HCl buffer (ph 7.1)/60 mM mannitol, 5 mM EGTA using a Potter Elvejhem homogenizer (Braun, Melsungen, 900 rpm, 10 strokes). Addition of 0.1 ml of 1 M $MgCl_2$ solution and incubation at 0° C. for 15 minutes was followed by centrifugation again at 3 000×g for 15 minutes. The supernatant was then centrifuged again at 46 000×g (20 000 rpm, SS-34 rotor) for 30 minutes. The precipitate was taken up in 30 ml of 20 mM Tris/Hepes buffer (pH 7.4)/280 mM mannitol and homogeneously resuspended by 20 strokes in a Potter Elvejhem homogenizer at 1 000 rpm. After centrifugation at 48 000×g (20 000 rpm, SS-34 rotor) for 30 minutes, the precipitate was taken up in 0.5 to 2 ml of Tris/Hepes buffer (pH 7.4)/280 mM mannitol (final concentration 20 mg/ml) and resuspended using a tuberculin syringe with a 27 gauge needle.

The vesicles were either used directly after preparation for labeling or transport studies or were stored at −196° C. in 4 mg portions in liquid nitrogen.

To prepare brush border membrane vesicles from rat small intestine, 6 to 10 male Wistar rats (bred at Kastengrund, Aventis Pharma) were sacrificed by cervical dislocation, and the small intestines were removed and rinsed with cold isotonic saline. The intestines were cut up and the mucosa was scraped off. The processing to isolate brush border membranes took place as described above. To remove cytoskeletal fractions, the brush border membrane vesicles from rat small intestine were treated with KSCN as chaotropic ion.

To prepare brush border membranes from rabbit small intestine, rabbits were sacrificed by intravenous injection of 0.5 ml of an aqueous solution of 2.5 mg of tetracaine HCl, 100 mg of m-butramide and 25 mg of mebezonium iodide. The small intestines were removed, rinsed with ice-cold physiological saline and frozen in plastic bags under nitrogen at −80° C. and stored for 4 to 12 weeks. For preparation of the membrane vesicles, the frozen intestines were thawed at 30° C. in a water bath and then the mucosa was scraped off. Processing to give membrane vesicles took place as described above.

To prepare brush border membrane vesicles from pig intestine, jejunum segments from a freshly slaughtered pig were rinsed with ice-cold isotonic saline and frozen in plastic bags under nitrogen at −80° C. Preparation of the membrane vesicles took place as described above.

Preparation of Brush Border Membrane Vesicles from the Renal Cortex of the Rat Kidney Brush border membrane vesicles were prepared from the cortex of the rat kidney by the method of Biber et al. The kidneys from 6 to 8 rats (200 to 250 g) were removed and the cortex was cut off each kidney as a layer about 1 mm thick. The kidneys were taken up in 30 ml of ice-cold 12 mM Tris/HCl buffer (pH 7.4)/300 mM mannitol and homogenized with an Ultraturrax shaft (level 180 V) for 4×30 seconds while cooling in ice. Addition of 42 ml of ice-cold distilled water was followed by addition of 850 µl of a 1 M $MgCl_2$ solution. Incubation at 0° C. for 15 minutes was followed by centrifugation at 4 500 rpm (Sorvall SS-34 rotor) for 15 minutes. The precipitate was discarded, and the supernatant was centrifuged at 16 000 rpm for 30 minutes. Resuspension of the precipitate in 60 ml of 6 mM Tris/HCl buffer (pH 7.4)/150 mM mannitol/2.5 mM EGTA by 10 strokes in a Potter-Elvejhem homogenizer (900) and addition of 720 µl of 1 mM $MgCl_2$ solution was followed by incubation at 0° C. for 15 minutes. The supernatant resulting after centrifugation at 4 500 rpm (SS-34 rotor) for 15 minutes was centrifuged at 16 000 rpm for 30 minutes. The supernatant was homogenized by 10 strokes in 60 ml of 20 mM Tris/Hepes buffer (pH 7.4)/280 mM mannitol, and the resulting suspension was then centrifuged at 20 000 rpm for 30 minutes. The precipitate was resuspended in 20 mM Tris/HCl buffer (pH 7.4)/280 mM mannitol using a tuberculin syringe with a 27 gauge needle and was adjusted to a protein concentration of 20 mg/ml.

Measurement of the glucose uptake by brush border membrane vesicles

The uptake of $[^{14}C]$-labeled glucose into brush border membrane vesicles was measured by the membrane filtration method. 10 µl of the brush border membrane vesicle suspension in 10 mM Tris/Hepes buffer (pH 7.4)/300 mM mannitol were added at 30° C. to 90 µl of a solution of 10 µM $[^{14}C]D$ glucose and the appropriate concentrations of the relevant inhibitors (5~200 µM) in 10 mM Tris/Hepes buffer (pH 7.4)/100 mM NaCl/100 mM.

After incubation for 15 seconds, the transport process was stopped by adding 1 ml of ice-cold stop solution (10 mM Tris/Hepes buffer (pH 7.4)/150 mM KCl) and the vesicle suspension was immediately filtered with suction through a cellulose nitrate membrane filter (0.45 µm, 25 mm diameter, Schleicher & Schüll) under a vacuum of from 25 to 35 mbar. The filter was washed with 5 ml of ice-cold stop solution. Each measurement was carried out as duplicate or triplicate determination. To measure the uptake of radiolabeled substrates, the membrane filter was dissolved in 4 ml of an appropriate scintilator (Quickszint 361, Zinsser Analytik GmbH, Frankfurt am Main), and the radioactivity was determined by liquid scintillation measurement. The measured values were obtained as dpm (disintegrations per minute) after calibration of the instrument using standard samples and after correction for any chemiluminescence present.

The active ingredients were compared for activity on the basis of $IC_{25}$ data obtained in the transport assay on rabbit renal cortex brush border membrane vesicles for selected substances. (The absolute values may be species- and experiment-dependent)

| Example No. | IC25 [µM] |
|---|---|
| 5* | 13.9 |
| 6* | 9.9 |
| 7* | 1.1 |
| 9* | 1.4 |
| 11* | 1.3 |
| 13* | 3.5 |
| 34* | 1.0 |
| 43* | 2.2 |
| 44* | 0.9 |
| 45* | 2.9 |
| 47* | 1.6 |
| 50* | 4.7 |
| 54* | 1.4 |
| 56* | 2.8 |

*β-D-gluco form

The preparation of various examples is described in detail hereinafter, and the other compounds of the formula I were obtained analogously:

EXPERIMENTAL PART

Example 1

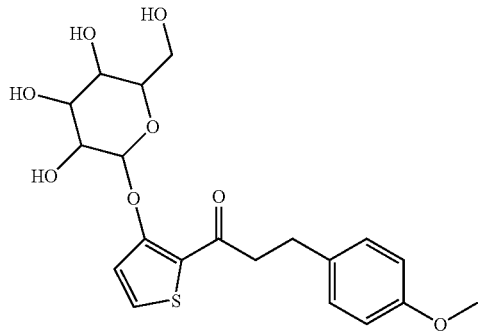

3-(4-Methoxy-phenyl)-1-[3-(3,4,5-trihydroxy-6-hydroxymethyl-tetrahydro-pyran-2-yloxy)-thiophen-2-yl]-propan-1-one

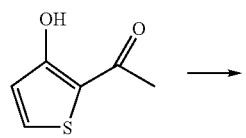

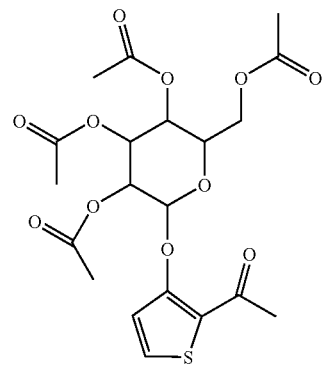

a) 4,5-Diacetoxy-6-acetoxymethyl-2-(2-acetyl-thiophen-3-yloxy)-tetrahydro-pyran-3-yl acetate 2 g of 1-(3-hydroxy-thiophen-2-yl)-ethanone were dissolved in 120 ml of dichloromethane and stirred with 6.4 g of 4,5-diacetoxy-6-acetoxymethyl-2-bromotetrahydropyran-3-yl acetate, 1.4 g of benzyltributylammonium chloride, 6.4 g of potassium carbonate and 1.2 ml of water at 22° C. for 20 h. Insoluble constituents were removed by filtration, the filtrate was concentrated and the crude product mixture was purified by column chromatograph (SiO$_2$, ethyl acetate/n-heptane=1:1). The product with the molecular weight of 472.5 ($C_{20}H_{24}O_{11}S$), MS (Cl): 473 (M+H$^+$) was obtained

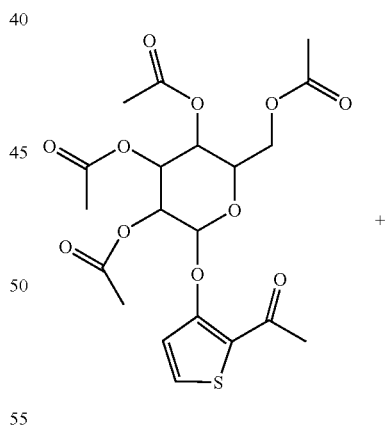

+

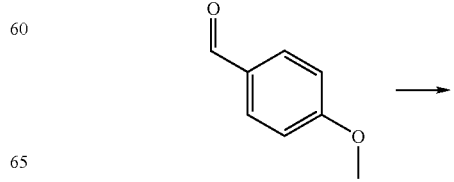

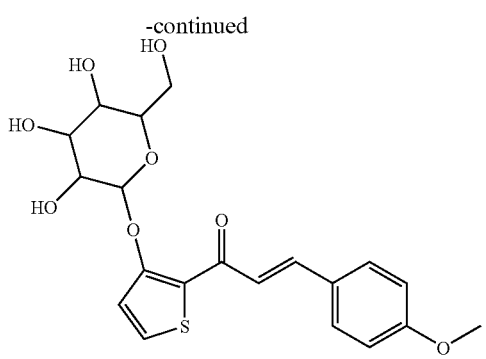

b) 3-(4-Methoxy-phenyl)-1-[3-(3,4,5-trihydroxy-6-hydroxymethyl-tetrahydro-pyran-2-yloxy)-thiophen-2-yl]-propenone 472 mg of 4,5-diacetoxy-6-acetoxymethyl-2-(2-acetyl-thiophen-3-yloxy)-tetrahydro-pyran-3-yl acetate were dissolved in 20 ml of methanol, and 5 ml of 1 N NaOCH$_3$ solution in methanol were added. 410 mg of 4-methoxy-benzaldehyde were added thereto, and the mixture was stirred at 22° C. for 20 h. The mixture was neutralized with a little dilute methanolic hydrochloric acid and concentrated, and the residue was purified by chromatography on a silica gel column (dichloromethane/methanol=6:1). The product with the molecular weight of 422.5 ($C_{20}H_{22}O_8S$), MS (ESI): 423 (M+H$^+$) was obtained.

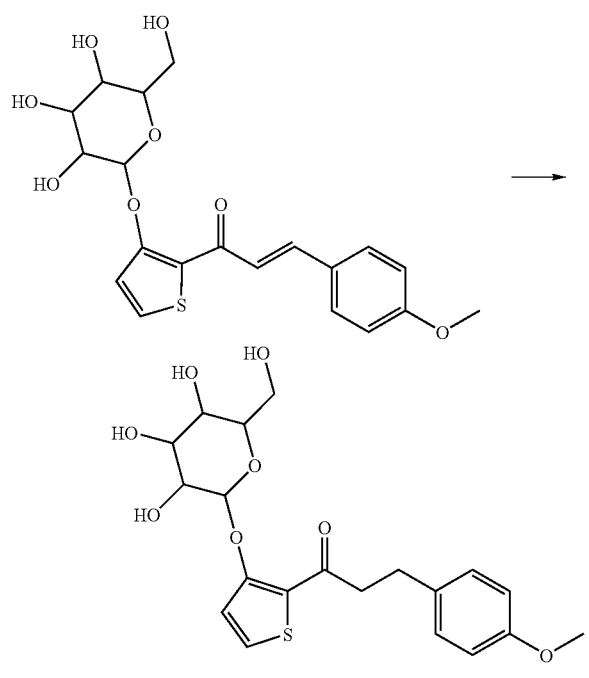

c) 3-(4-Methoxy-phenyl)-1-[3-(3,4,5-trihydroxy-6-hydroxymethyl-tetrahydro-pyran-2-yloxy)-thiophen-2-yl]-propan-1-one 100 mg of 3-(4-methoxy-phenyl)-1-[3-(3,4,5-trihydroxy-6-hydroxymethyl-tetrahydro-pyran-2-yloxy)-thiophen-2-yl]-propenone were hydrogenated dissolved in 10 ml of ethanol with about 20 mg of 5% palladium on carbon in a shaking apparatus under slightly elevated pressure (about 4 h, TLC check). The catalyst was filtered off, the filtrate was concentrated, and the residue was purified by column filtration (SiO$_2$, dichloromethane/methanol=6:1). The product with the molecular weight of 424.5 ($C_{20}H_{24}O_8S$), MS (ESI): 447 (M+Na$^+$) was obtained.

α-D-Acetobromoglucose was used as 4,5-diacetoxy-6-acetoxymethyl-2-bromotetrahydropyran-3-yl acetate in the synthetic sequence described above. Here the glycoside of Example 1 was obtained in β-D-gluco form. This was also applied to the examples given below. Use of α-D-acetobromogalactose results in the glycoside in the β-D-galacto form, use of α-D-acetobromoallose results in the glycoside in the β-D-allo form or use of β-D-acetobromomannose results in the glycoside in α-D-manno form.

The following exemplary substances 2 to 6 were prepared by the same synthetic route as described above in Example 1:

| Example | A | Ar | MS or LC/MS |
|---|---|---|---|
| 2 | (propanone) | benzo[1,4]dioxane | OK |
| 3 | (propanone) | benzo[1,3]dioxole | OK |
| 4 | (propanone) | benzofuran | OK |
| 5 | (propanone) | thiophen-3-yl | OK |
| 6 | (propanone) | thiophen-2-yl | OK |

Example 7

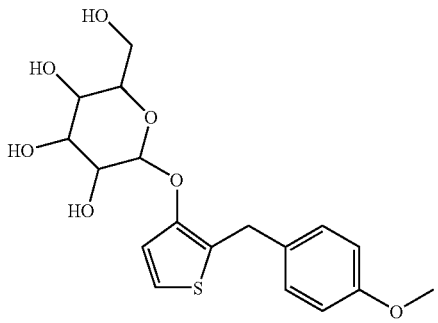

2-Hydroxymethl-6-[2-(4-methoxy-benzyl)-thiophen-3-yloxy]-tetrahydro-pyran-3,4,5-triol

Example 8

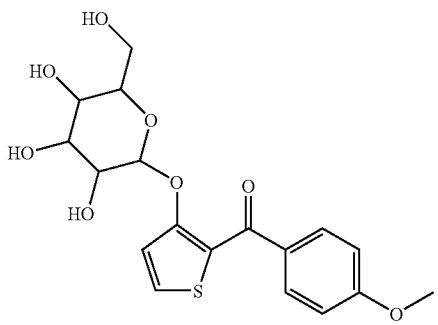

(4-Methoxy-phenyl)-[3-(3,4,5-trihydroxy-6-hydroxymethyl-tetrahydro-pyran-2-yloxy)-thiophen-2-yl]-methanone

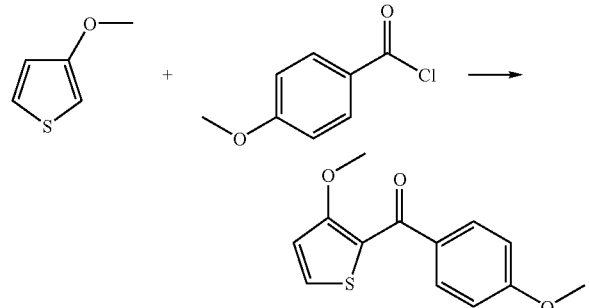

(4-Methoxy-phenyl)-(3-methoxy-thiophen-2-yl)-methanone 2.7 ml of tin tetrachloride were added to a solution of 2.3 g of 3-methoxy-thiophene and 3.4 g of 4-methoxybenzoyl chloride in 50 ml of dichloromethane while cooling in ice. The mixture was stirred at room temp. overnight. For workup, 75 ml of 2 hydrochloric acid were added and the mixture was extracted three times with dichloromethane. The combined organic phases were washed twice with each of 2 N sodium carbonate solution and water, and then the solvent was removed in vacuo, and the crude product was purified by column filtration (SiO$_2$, ethyl acetate/n-heptane=1:2). The product with the molecular weight of 248.3 (C$_{13}$H$_{12}$O$_3$S), MS (Cl): 249 (M+H$^+$) was obtained.

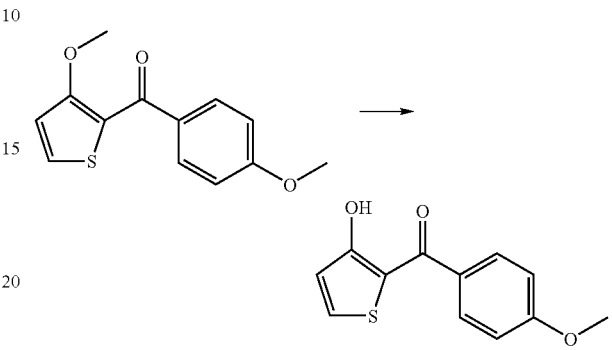

b) (3-Hydroxy-thiophen-2-yl)-(4-methoxy-phenyl)-methanone 993 mg of (4-methoxy-phenyl)-(3-methoxy-thiophen-2-yl)-methanone were dissolved in 20 ml of dry dichloromethane, and 7 ml of boron tribromide/dimethyl sulfide complex were added. The mixture was stirred at room temp. until the reaction was complete (TLC check). It was then poured into water and extracted several times with dichloromethane. The organic phase was dried and concentrated, and the residue was purified by column chromatography (SiO$_2$, ethyl acetate/n-heptane=1:4). The product with the molecular weight of 234.3 (C$_{12}$H$_{10}$O$_3$S), MS (Cl): 235 (M+H$^+$) was obtained.

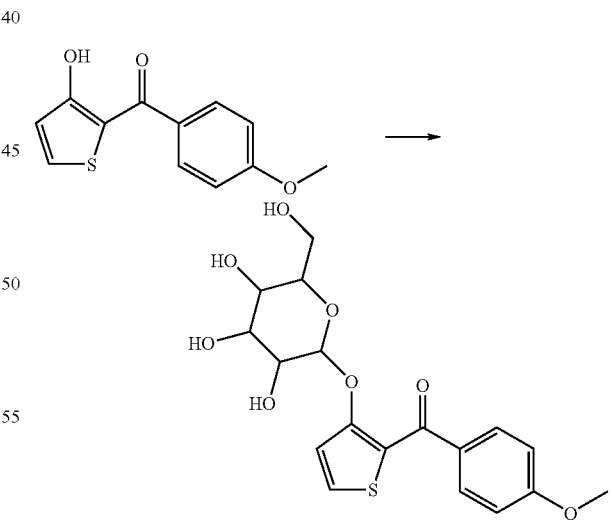

c) (4-Methoxy-phenyl)-[3-(3,4,5-trihydroxy-6-hydroxymethyl-tetrahydro-pyran-2-yloxy)-thiphen-2-yl]-methanone=Example 8

2.8 g of (3-hydroxythiophen-2-yl)-(4-methoxy-phenyl)-methanone were dissolved in 350 ml of dichloromethane, and 12.64 g of 3,4,5-triacetoxy-6-bromo-tetrahydropyran-2-ylmethyl actate, 15.4 g of potassium carbonate, 3.6 g of benzyltributylamonium chloride and finally 3 ml of water were added. The mixture was vigorously stirred at room temp. for 20 h. After the reaction was complete, the residue after filtration and concentration was filtered through $SiO_2$ with ethyl acetate/heptane'1:2. The solvent was removed and the residue was taken up in about 300 ml of methanol and, after addition of 35 ml of 1 N $NaOCH_3$ solution in methanol, stirred at room temp. for 1 h. This was followed by neutralization with 7% methanolic hydrochloric acid (about 35 ml), addition of about 100 of dichloromethane/methanol/conc. ammonia=30:5:0.1 mobile phase mixture and stirring for 5 min. This was followed by concentration, taking up the residue with the same mobile phase mixture and removing insoluble salt from the solution. Chromatography on silica gel results in the product with the molecular weight of 396.42 ($C_{18}H_{20}O_8S$), MS (ESI): 397 (M+H$^+$), 235 (M+H$^+$-gluc).

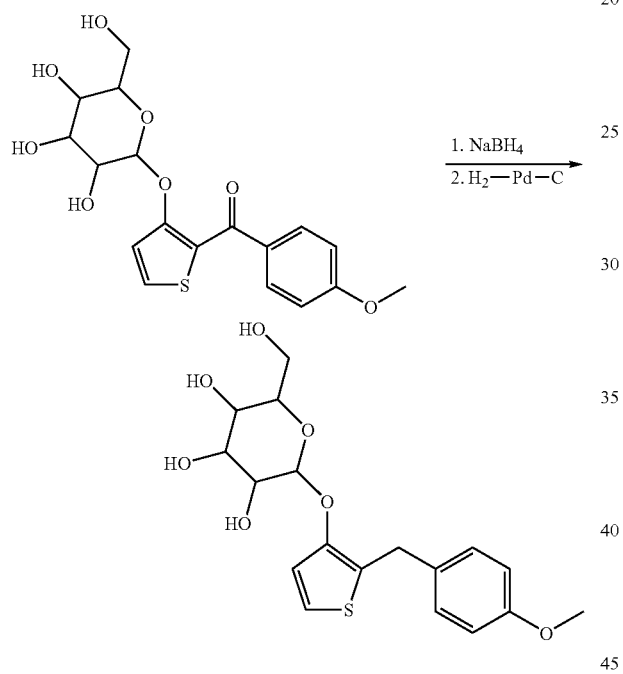

d) 2-Hydroxymethyl-6-[2-(4-methoxy-benzyl)-thiophen-3-yloxy]-tetrahydro-pyran-3,4,5-triol=Example 7

4.1 g of (4-methoxy-phenyl)-[3-(3,4,5-trihydroxy-6-hydroxymethyl-tetrahydro-pyran-2-yloxy)-thiophen-2-yl]-methanone were dissolved in 200 ml of tetrahydrofuran+20 ml of methanol, and 500 mg of sodium borohydride were added. After the reaction was complete (TLC check, dichloromethane/methanol/conc. ammonia=30:5:0.1; about 30-60 min), water was added and the mixture was extracted three times with ethyl actetate. The combined organic phases were dried over magnesium sulfate and concentrated. 2{2-[Hydroxy-(4-methoxy-phenyl)-methyl]-thiophen-3-yloxy}-6-hydroxymethyl-tetrahydro-pyran-3,4,5-triol was obtained as crude product which was purified by filtration through silica gel.

The entire amount was dissolved in about 800 ml of dry ethanol, and the solution was saturated with argon in a shaking apparatus. Then dry palladium on carbon was added as catalyst, and the mixture was hydrogenated while shaking vigorously at 22° C. and atmospheric pressure for 6-7 h. After the reaction was complete, the mixture was filtered with suction through a clarifying layer, and the solvent was removed in vacuo. The residue was purified by column chromatography ($SiO_2$, dichloromethane/methanol=9:1). (TLC plates developed with 10% sulfuric acid). The product with the molecular weight of 382.44 ($C_{18}H_{22}O_7S$), MS (ESI): 383 (M+H$^+$-gluc) was obtained.

Alternatively, this compound can also be prepared in the following way:

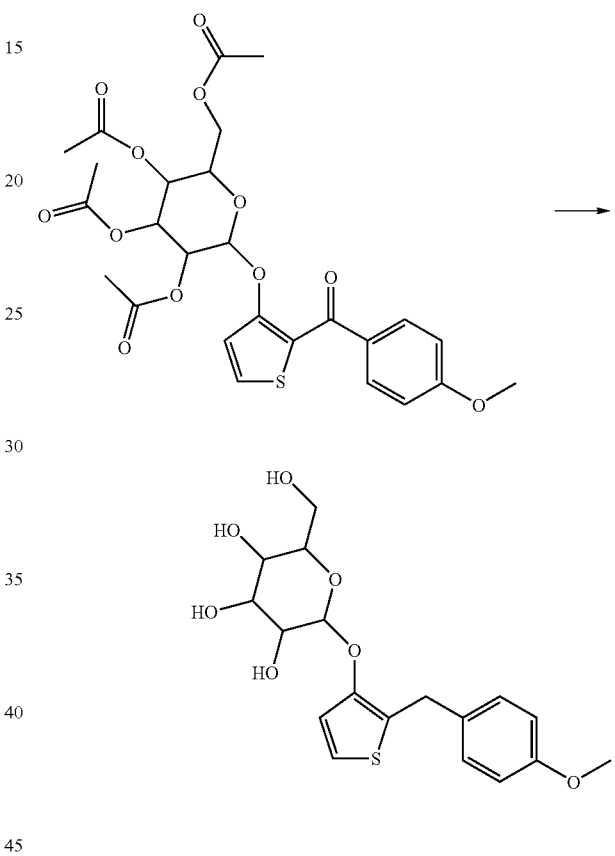

226 mg of 3,4,5-triacetoxy-6-[2-(4-methoxy-benzyl)-thiophen-3-yloxy]-tetrahydro-pyran-2-yl-methyl acetate were dissolved in 4 ml of acetonitrile and cooled to 0° C. in an ice bath. 0.3 ml of trimethylchlorosilane and 151 mg of sodium cyanoborohydride were added, the ice bath was removed, and the reaction was stirred for 2 h. The reaction mixture was diluted with 30 ml of dichloromethane and filtered through Celite, and the organic phase was washed with 20 ml of saturated sodium bicarbonate solution and 20 ml of sodium chloride solution. The residue was purified by column chromatography ($SiO_2$, ethyl acetate/n-heptane=1:2). The crude product was taken up in methanol, and 1 ml of sodium methanolate solution (10 mg/ml in methanol) was added. The solution was stirred at 22° C. for 18 h and, after addition of Amberlyst 15 (H$^+$ form), diluted with 10 ml of methanol and filtered. The residue was washed with 20 ml of methanol, the organic phase was concentrated and the residue was chromatographed on silica gel. 120 mg of the product with the molecular weight of 382.44 ($C_{18}H_{22}O_7S$), MS (ESI): 400 (M+NH$_4^+$) were obtained.

Preparation of (3-methoxy-thiophen-2-yl)-(4-nitro-phenyl)-methanone:

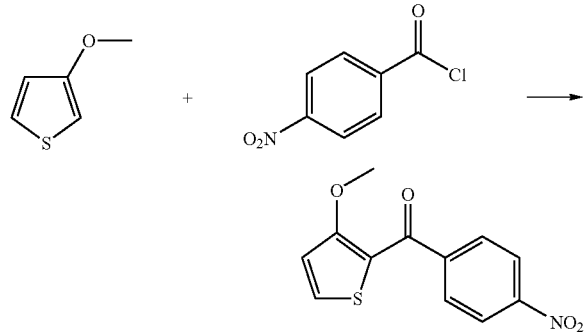

0.5 ml of 3-methoxythiophene was dissolved in 50 ml of dichloromethane. 968 mg of 4-nitrobenzoyl chloride were added, and the reaction mixture was cooled to 0° C. in an ice bath. Then 696 mg of aluminum trichloride were added and the reaction was stirred at 0° C. for 4 h. The reaction mixture was added to 100 ml of ice-water and stirred for 15 min, and 100 ml of dichloromethane were added. The organic phase was separated off, washed with 50 ml of 0.5 molar sodium hydroxide solution and 50 ml of saturated sodium chloride solution, dried over sodium sulfate and concentrated. The resulting mixture was then purified by column chromatography (SiO$_2$, ethyl actate/n-heptane). The product with the molecular weight of 263.27 (C$_{12}$H$_9$NO$_4$S); MS (CI): 264.25 (M+H$^+$) was obtained.

(3-Methoxy-thiophen-2-yl)-(4-nitro-phenyl)-methanone was then converted as described by way of example for example 7 into exemplary substance 16.

The following exemplary substances 9 to 34 were prepared by the same synthetic route:

| Example | A | Ar | MS or LC/MS |
|---------|------|-----|-------------|
| 9 | CH$_2$ | phenyl | OK |
| 10 | CHOH | phenyl | OK |
| 11 | CH$_2$ | 4-ethoxyphenyl | OK |
| 12 | CH$_2$ | 3,4-dimethoxyphenyl | OK |
| 13 | CH$_2$ | 4-(OC$_7$H$_{10}$)phenyl | OK |
| 14 | CH$_2$ | 4-fluorophenyl | OK |
| 15 | CH$_2$ | 4-iodophenyl | OK |
| 16 | CH$_2$ | 4-nitrophenyl | OK |
| 17 | CH$_2$ | 4-methylphenyl | OK |
| 16 | CH$_2$ | 3-methylphenyl | OK |
| 19 | CH$_2$ | 2-methylphenyl | OK |
| 20 | CH$_2$ | 4-ethylphenyl | OK |

-continued

| Example | A | Ar | MS or LC/MS |
|---------|-----|-----|-------------|
| 21 | CH₂ | 2,6-dimethyl-4-methoxyphenyl | OK |
| 22 | CH₂ | 2,2-difluoro-1,3-benzodioxol-5-yl | OK |
| 23 | CH₂ | 4-propylphenyl | OK |
| 24 | CH₂ | 4-tert-butylphenyl | OK |
| 25 | CH₂ | 4-hydroxyphenyl | OK |
| 26 | CH₂ | 4-benzyloxyphenyl | OK |
| 27 | CH₂ | thiophen-3-yl | OK |
| 28 | CH₂ | benzothiophen-2-yl | OK |
| 29 | CH₂ | 3-methoxyphenyl | OK |
| 30 | CH₂ | 4-cyanophenyl | OK |
| 31 | CH₂ | 1,3-benzodioxol-5-yl | OK |
| 32 | CH₂ | 4-methylthiophenyl | OK |
| 33 | CH₂ | 4-butoxyphenyl | OK |
| 34 | CH₂ | 4-trifluoromethoxyphenyl | OK |

The indication MS/LCMS is Ok means that the molecular peak of the indicated compound was obtained as M+1 (MH⁺) and/or as M+18 (MNH₄⁺) and/or M+23 (MNa⁺).

Example 35

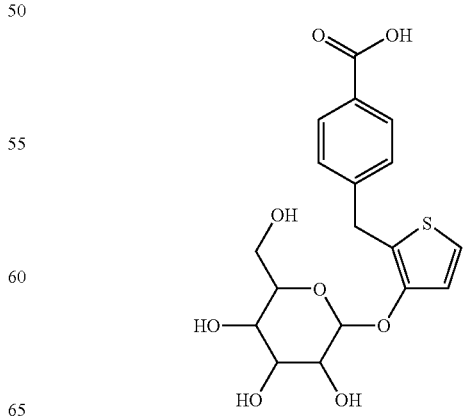

4-[3-(3,4,5-Trihydroxy-6-hydroxymethyl-tetrahydro-pyran-2-yloxy)-thiophen-2-ylmethyl]-benzoic acid 46 mg of 4-[3(3,4,5-trihydroxy-6-hydroxymethyl-tetrahydro-pyran-2-yloxy)-thiophen-2-ylmethyl]-benzonitrile were dissolved in a mixture of 5 ml of methanol and 2 ml of 25% strength potassium hydroxide solution and heated at 70° for 3 h. The solution was diluted with 10 ml of water and neutralized with 2 N HCl. The resulting solution was freeze dried. The crude product was then purified by column chromatography (SiO$_2$, dichloromethane/methanol/acetic acid/water=8:2:0.1:0.1). 45 mg of the product with the molecular weight of 396.42 (C$_{18}$H$_{20}$O$_8$S), MS (ESI): 414.45 (M+NH$_4^+$) were obtained.

Example 36

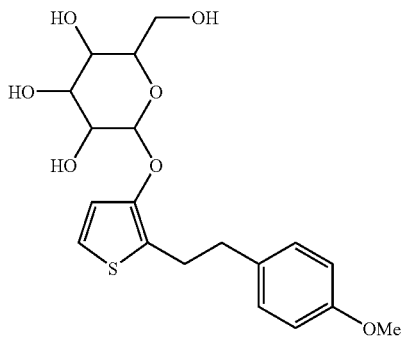

2-Hydroxymethyl-6-{2-[2-(4-methoxy-phenyl)-ethyl]-thiophen-3-yloxy}-tetrahydro-pyran-3,4,5-triol Example 37

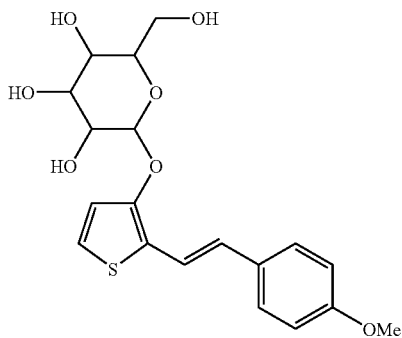

2-Hydroxymethyl-6-{2-[2-(4-methoxy-phenyl)-vinyl]-thiophen-3-yloxy}-tetrahydro-pyran-3,4,5-triol

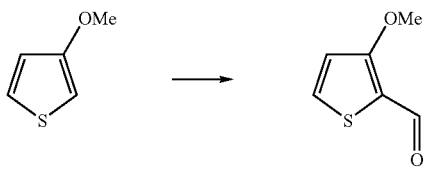

a) 3-Methoxy-thiophene-2-carbaldehyde 1.03 ml of 3-methoxythiophene were dissolved in 2.3 ml of dimethylformamide. While cooling in ice, 1.06 ml of phosphoryl chloride were added. After 1 h, the reaction solution was added to ice, and the solution was neutralized with 5 molar sodium hydroxide solution. The aqueous phase was extracted 3 times with 25 ml of diethyl ether each time, and the combined organic phases were then washed with 50 ml of saturated sodium chloride solution, dried over sodium sulfate and concentrated. 840 mg of the product with the molecular mass of 142.18 (C$_6$H$_7$O$_2$S) were obtained. MS (ESI): 143.0 (M+H$^+$).

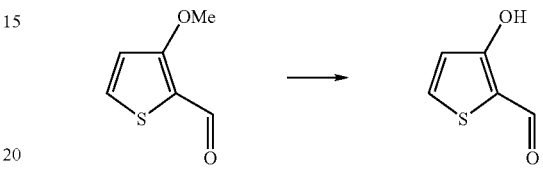

b) 3-Hydroxy-thiophen-2-carbaldehyde 200 mg of 3-methoxy-thiophene-2-carbaldehyde were dissolved in 5 ml of dichloromethane. 880 mg of boron tribromide-dimethyl sulfidecomplex were dissolved in 5 ml of dichloromethane and added to the reaction solution. The solution was stirred for 18 h. The reaction mixture was poured into 30 ml of water, and the mixture was extracted 4 times with 20 ml of dichloromethane each time. The combined organic phases were washed with 30 ml of saturated sodium chloride solution, dried over sodium sulfate and concentrated. 140 mg of 3-hdyroxy-thiophene-2-carbaldehyde with the molecular weight of 128.15 (C$_5$H$_4$O$_2$S) were obtained. MS (ESI): 129.0 (M+H$^+$)

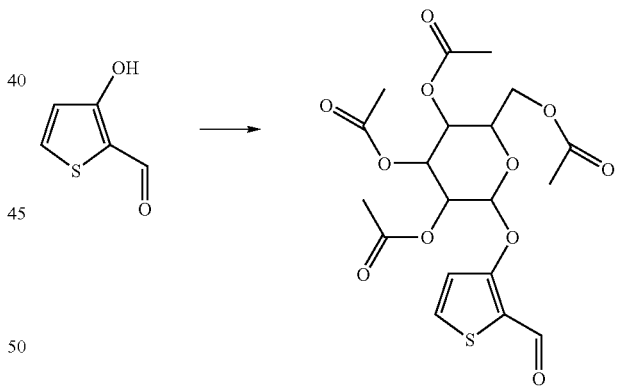

c) 4,5-Diacetoxy-6-acetoxymethyl-2-(2-formyl-thiophen-3-yloxy)-tetrahydropyran-3-yl acetate 3.81 g of 3-hydroxy-thiophene-2-carbaldehyde, 30.5 g of (4,5-diacetoxy-6-acetoxymethyl-2-[5-isopropyl-2-(4-methoxy-benzoyl)-thiophen-3-yloxy]-tetrahydro-pyran-3-yl) actate, 37.0 g of potassium carbonate and 9.2 g of benzyltributylammonium chloride were dissolved in 850 ml of dichloromethane. 7.5 ml of water were added, and the reaction mixture was stirred for 60 h. The solution was extraced with water and saturated sodium chloride solution, and the organic phase was dried over sodium sulfate and evaporated. 60 ml of ethanol:water (9:1) were added to the resulting brownish foam, and the resulting fine precipitate was filtered off with suction. The product with the molecular weight: 458.44 ($C_{19}H_{22}O_{11}S$), MS (ESI): 476 ($M+NH_4^+$) was obtained.

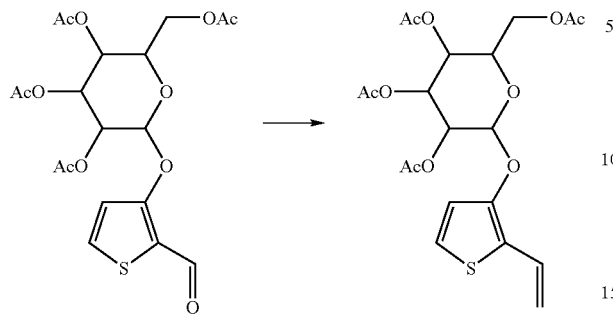

d) 3,4,5-Triacetoxy-6-(2-vinyl-thiophen-3-yloxy)-tetrahydropyran-2-ylmethyl actate 3.30 g of 3,4,5-triacetoxy-6-(2-formyl-thiophen-3-yloxy)-tetrahydropyran-2-ylmethyl actate were dissolved in 60 ml of dioxane. 6.43 g of methyltriphenylphosphonium bromide, 5.37 g of potassium carbonate and 0.25 ml of water were added, and the solution was refluxed for 4 h. The solution was concentrated and purified by column filtration. 2.89 g of the product with the molecular weight: 456.47 ($C_{20}H_{24}O_{10}S$), MS (ESI): 479.10 ($M+Na^+$); 474.10 ($M+NH_4^+$) were obtained.

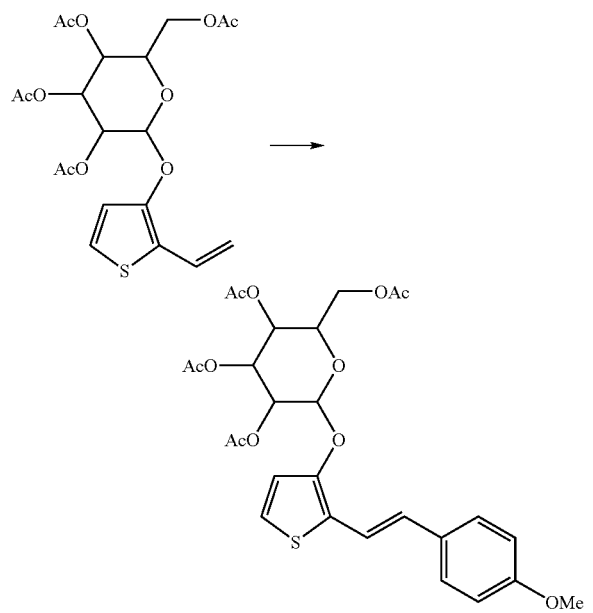

e) 3,4,5-Triacetoxy-6-{2-[2-(4-methoxy-phenyl)-vinyl]-thiophen-3-yloxy}-tetrahydropyran-2-ylmethyl acetate 148 mg of 3,4,5-triacetoxy-6-(2-vinyl-thiophen-3-yloxy)-tetrahydropyran-2-ylmethyl acetate were dissolved in 2 ml of dichloromethane under argon. Tricyclohexyphosphine-[1,3-bis(2,4,6-trimethylphenyl)-4,5-dihydroimidazol-2-ylidene][benzylidene]ruthenium(IV) dichloride (23 mg, dissolved in 2 ml of dichloromethane) was added, and the solution was heated under reflux for 8 h. The reaction solution was concentrated and purified by column chromatography ($SiO_2$, heptane/ethyl acetate 2:1). 132 mg of the product with the molecular mass of 562.60 ($C_{27}H_{30}O_{11}S$) were obtained. MS(ESI): 575.20 ($M+Na^+$).

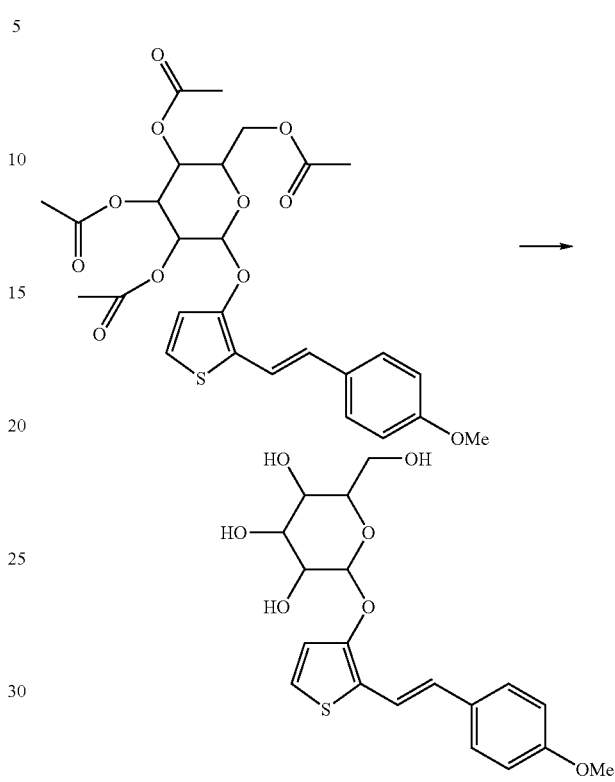

f) 2-Hydroxymethyl-6-{2-[2-(4-methoxy-phenyl)-vinyl]-thiophen-3-yloxy}-tetrahydro-pyran-3,4,5-triol=Example 37

150 mg of 3,4,5-triacetoxy-6-{2-[2-(4-methoxy-phenyl)-vinyl]-thiophen-3-yloxy}-tetrahydropyran-2-ylmethyl acetate were suspended in 10 ml of dry methanol. 1.0 ml of a methanolic NaOMe solution (10 mg/ml) was added. The solution was stirred at 22° C. for 18 h. Amberlyst 15 ($H^+$ form) was added and the solution was diluted with 10 ml of MeOH and filtered, and the residue was washed with 20 ml of methanol. The organic phase was concentrated, and the residue was purified by chromatography on silica gel. 100 mg of the product with the molecular weight: 394.45 ($C_{19}H_{22}O_7S$), MS (ESI): 417 ($M+Na^+$); 412 ($M+NH_4^+$) were obtained.

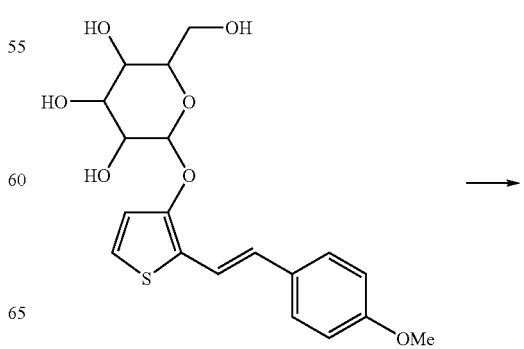

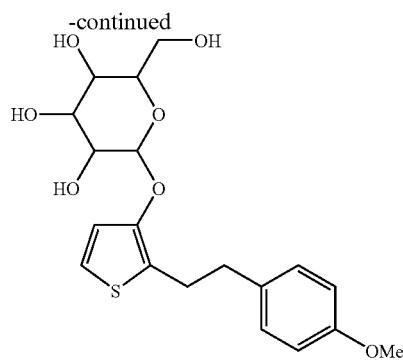

g) 2-Hydroxymethyl-6-{2-[2-(4-methoxy-phenyl)-ethyl]-thiophen-3-yloxy}-tetrahydro-pyran-3,4,5-triol=Example 36

50 mg 2-hydroxymethyl-6-{2-[2-(4-methoxy-phenyl)-vinyl]-thiophen-3-yloxy}-tetrahydro-pyran-3,4,5-triol were dissolved in 10 of methanol. 20 mg of palladium on activated carbon were added and the solution was stirred under a hydrogen atmosphere for 18 h. The catalyst was filtered off and washed with 60 ml of methanol, and the organic phase was concentrated. The residue was chromatographed on silica gel (ethyl acetate). 18 mg of the product with the molecular weight of 396.46 ($C_{19}H_{24})_7S$); MS (ESI): 419.05 (M+Na$^+$), 414.10 (M+NH$_4^+$).

The following exemplary substances 38 to 50 were prepared by the same synthetic route.

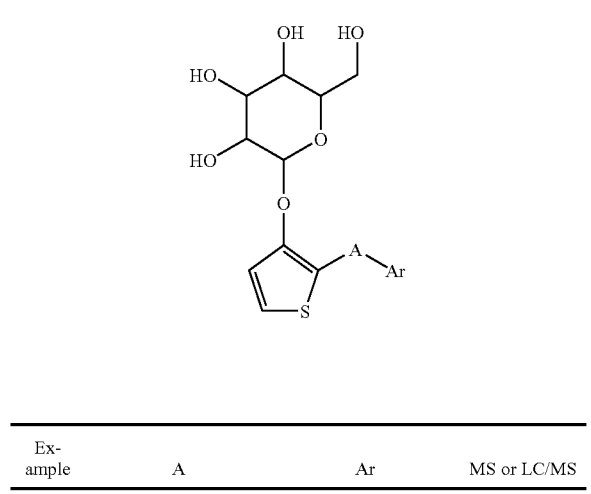

| Example | A | Ar | MS or LC/MS |
|---|---|---|---|
| 38 | —CH=CH— | 4-F-C6H4 | OK |
| 39 | —CH=CH— | 4-Cl-C6H4 | OK |
| 40 | —CH=CH— | 4-OEt-C6H4 | OK |
| 41 | —CH=CH— | 4-Me-C6H4 | OK |
| 42 | —CH=CH— | 4-OH-C6H4 | OK |
| 43 | —CH2—CH2— | 4-F-C6H4 | OK |
| 44 | —CH2—CH2— | 4-Cl-C6H4 | OK |
| 45 | —CH2—CH2— | 4-OEt-C6H4 | OK |
| 46 | —CH2—CH2— | 4-Me-C6H4 | OK |
| 47 | —CH2—CH2— | 4-OH-C6H4 | OK |
| 48 | —CH=CH—CH2— | 4-OMe-C6H4 | OK |
| 49 | —CH2—CH2—CH2— | 4-OMe-C6H4 | OK |
| 50 | —CH=CH—CH2— | 3,4-methylenedioxyphenyl | OK |

The indication MS/LCMS is OK means that the molecular peak of the indicated compound was obtained as M+1 (MH⁺) and/or as M+18 (MNH$_4^+$) and/or M+23 (MNA⁺).

Example 51

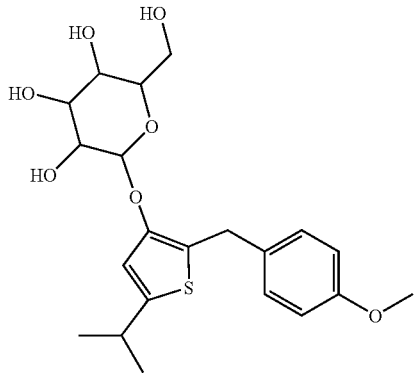

2-Hydroxymethyl-6-[5-isopropyl-2-(4-methoxy-benzyl)-thiophen-3-yloxy]-tetrahydro-pyran-3,4,5-triol

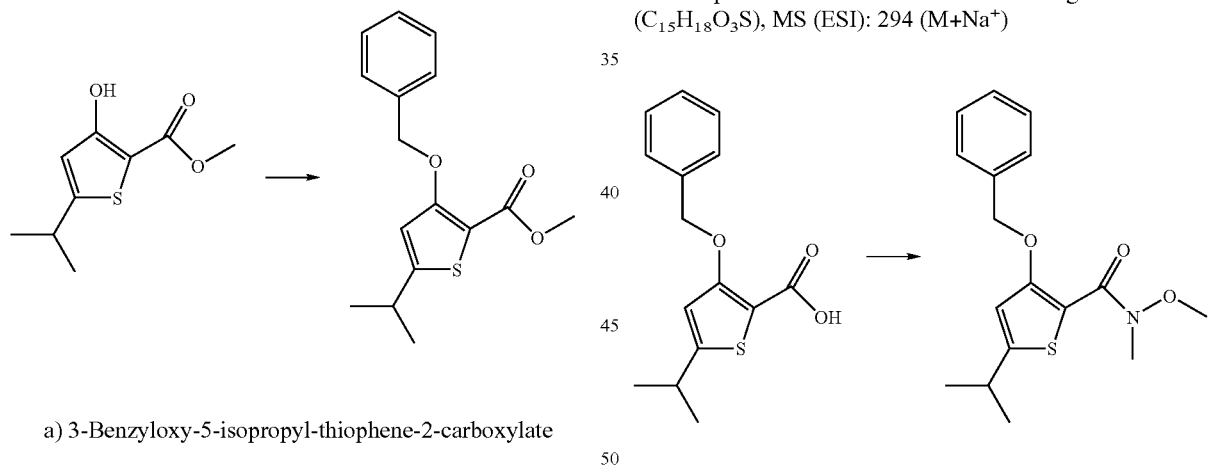

a) 3-Benzyloxy-5-isopropyl-thiophene-2-carboxylate 1.16 g of methyl 3-hydroxy-5-isopropyl-thiophene-2-carboxylate, which were synthesized by a process known from the literature [H. Fiesselmann, F. Thomas, Chem. Ber. 1956, 89, 1907], were dissolved in 25 ml of dimethylformamide (DMF), and 2.83 g of cesium carbonate and 1.72 ml of benzyl bromide were added. The reaction mixture was stirred at 22° C. for 72 h. Then 10 ml of methanol were added and, after 30 min, 100 ml of saturated sodium bicarbonate solution and 50 of water were added. The mixture was extracted 3 times with 70 ml of diethyl ether each time. The combined organic phases were dried over sodium sulfate and concentrated. The crude product was purified by column chromatography (SiO$_2$, ethyl acetate/n-heptaine=1:4).

The product was with the molecular weight of 290.4 (C$_{16}$H$_{18}$O$_3$S), MS (ESI): 291 (M+H⁺) was obtained.

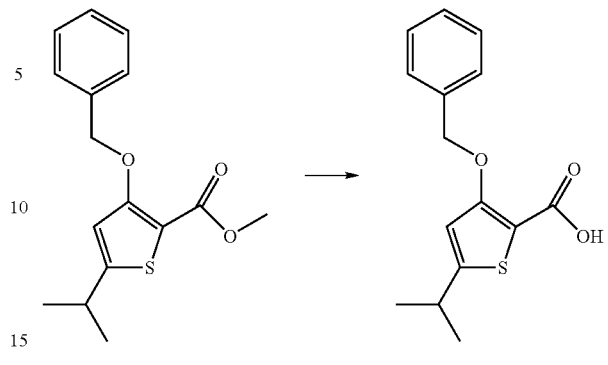

b) 3-Benzyloxy-5-isopropyl-thiophene-2-carboxylic acid 1.16 g of methyl 3-benzyloxy-5-isopropyl-thiophene-2-carboxylate were dissolved in 10 ml of tetrahydrofuran (THF) and 10 ml of methanol, and a solution of 1.7 g of lithium hydroxide in 10 ml of water was added. The reaction mixture was stirred at 22° C. for 72 h. Methanol and THF were stripped off in the rotary evaporator. While cooling in ice, the reaction mixture was adjusted to pH=4 with 2 molar hydrochloric acid and extracted twice with 50 ml of ethyl acetate each time. The combined organic phases were dried over sodium sulfate and concentrated.

The product with the molecular weight of 276.4 (C$_{15}$H$_{18}$O$_3$S), MS (ESI): 294 (M+Na⁺)

c) 3-Benzyloxy-5-isopropyl-N-methoxy-N-methylthiophene-2-carboxamide 860 mg of 3-benzyloxy-5-isopropyl-thiophene-2-carboxylic acid were dissolved in 30 ml of dichloromethane, and 560 mg of N,O-dimethylhydroxylamine hydrochloride and 2.3 of triethylamine were added. After 15 min at 22° C., 2.3 ml of a 50% strength 1-propanephosphonic anhydride solution in acetic acid were added, and the mixture was stirred at 22° C. for a further 18 h. The reaction mixture was washed twice with 20 ml of water each time and once with 70 ml of saturated sodium chloride solution. The organic phase was dried over sodium sulfate and concentrated.

The product with the molecular weight of 319.4 (C$_{17}$H$_{21}$NO$_3$S), MS (ESI): 320 (M+H⁺) was obtained.

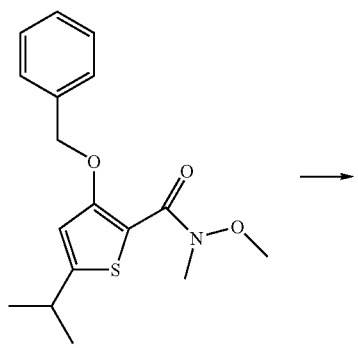

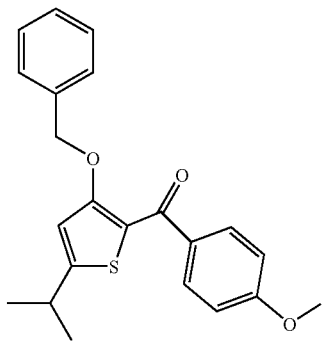

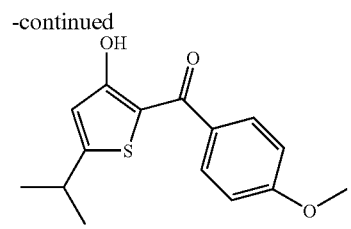

e) (3-Hydroxy-5-isopropyl-thiophen-2-yl)-(4-methoxy-phenyl)-methanone 1.00 g of (3-benzyloxy-5-isopropyl-thiophen-2-yl)-(4-methoxy-phenyl)-methanone was dissolved in 20 ml of dichloromethane. 2.73 ml of a 1 molar solution of boron tribromide-dimethyl sulfide complex in dichloromethane were added to the reaction solution. The solution was stirred at 22° C. for 1.5 h. The reaction mixture was poured into 50 ml of water, and the mixture was extracted twice with 30 ml of dichloromethane each time. The combined organic phase was extracted twice with 30 ml of saturated sodium bicarbonate solution each time and washed one with 50 ml of saturated sodium chloride solution, dried over sodium sulfate and concentrated. The crude product was purified by column chromatography (SiO2, ethyl acetate/n-heptane=1:4).

The product with the molecular weight of 276.4 ($C_{15}H_{16}O_3S$), MS (ESI): 299 (M+Na$^+$) was obtained.

d) (3-Benzyloxy-5-isopropyl-thiophen-2-yl)-(4-methoxy-phenyl)-methanone 860 mg of 3-benzyloxy-5-isopropyl-N-methoxy-N-methylthiophene-2-carboxamide were dissolved in 50 ml of tetrahydrofuran (THF) and cooled to 0> C. in an ice bath, and 31.3 ml of 0.5 molar 4-methoxyphenymagnesium bromide solution in tetrahydrofuran were added. After 30 min, the ice bath was removed and the reaction mixture was warmed to 22° C. After one hour, 70 ml of saturated sodium bicarbonate solution were added to the reaction mixture, and it was extracted twice with 100 ml of methyl acetate each time. The combined organic phases were washed with 70 ml of saturated sodium chloride solution, dried over sodium sulfate and concentrated. The crude product was purified by column chromatography (SiO$_2$, ethyl acetate/n-heptane=1:3).

The product with the molecular weight of 366.5 ($C_{22}H_{22}O_3S$), MS (ESI): 367 (M+H$^+$) was obtained.

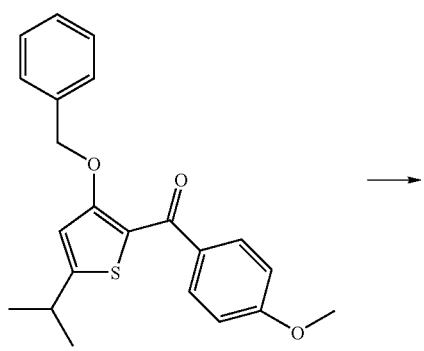

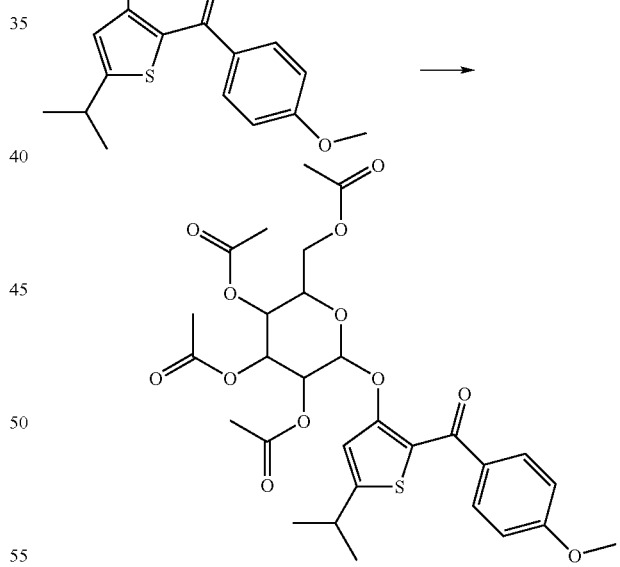

f) (4,5-Diacetoxy-6-acetoxymethyl-2-[5-isopropyl-2-(4-methoxy-benzoyl)-thiophen-3-yloxy]-tetrahydropyran-3yl) acetate 380 mg of (3-hydroxy-5-isopropyl-thiophen-2-yl)-(4-methoxy-phenyl)-methanone, 848 mg of 4,5-diacetoxy-6-acetoxymethyl-2-bromo-tetrahydro-pyran-3-yl acetate, 1.43 g of potassium carbonate and 71.1 mg of benzyltributylammonium chloride were dissolved in 20 ml of dichloromethane, and 1.20 ml of water were added. The reaction mixture was stirred at 22° C. for 40 h. 50 ml of water were added to the reaction mixture, which was extracted twice with 50 ml of dichloromethane each time. The combined organic phases were washed with 50 ml of saturated sodium chloride solution, dried over sodium sulfate and concentrated. The crude product was purified by column chromatography (SiO$_2$, ethyl acetate/n-heptane=1:1).

The product with the molecular weight of 606.7 ($C_{29}H_{34}O_{12}S$), MS (ESI): 607 (M+H$^+$) was obtained.

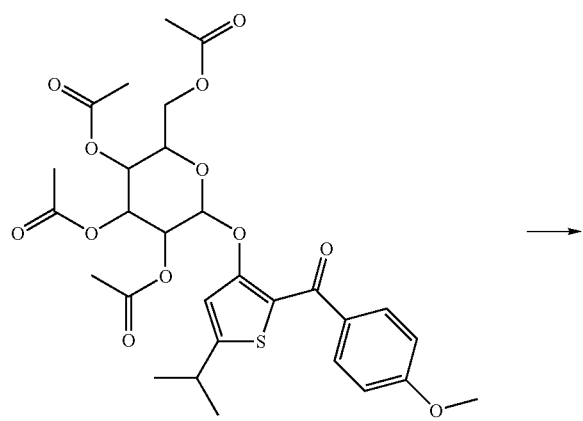

g) (4,5-Diacetoxy-6-acetoxymethyl-2-[5-isopropyl-2-(4-methoxy-benzyl)-thiophen-3-yloxy]-tetrahydro-pyran-3-yl) acetate 630 mg of (4,5-diacetoxy-6-acetoxymethyl-2-[5-isopropyl-2-(4-methoxy-benzoyl)-thiophen-3-yloxy]-tetrahydro-pyran-3-yl) acetate were dissolved in 30 ml of acetonitrile and cooled to 0° C. in an ice bath. 1.31 ml of trimethylchlorosilane and 652 mg of sodium cyanoborohydride were added, the ice bath was removed and the reaction was stirred for 2 h. 100 ml of water were added to the reaction mixture, which was extracted twice with 70 ml of dichloromethane each time. The combined organic phases were washed with 50 ml of saturated sodium chloride solution, dried over sodium sulfate and concentrated. The crude product was purified by column chromatography (SiO$_2$, ethyl acetate/n-heptane=1:1).

The product with the molecular weight of 592.7 ($C_{29}H_{36}O_{11}S$), MS (ESI): 593 (M+H$^+$) was obtained.

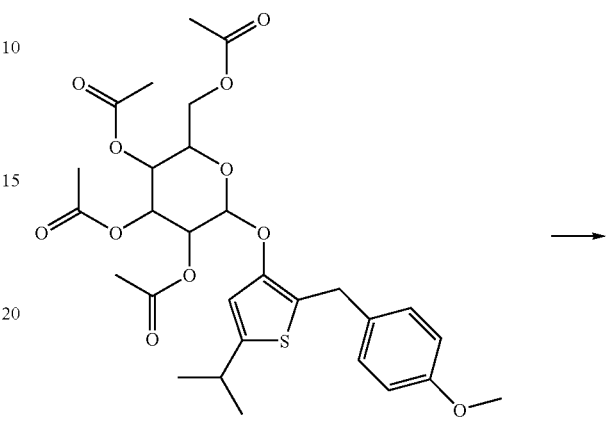

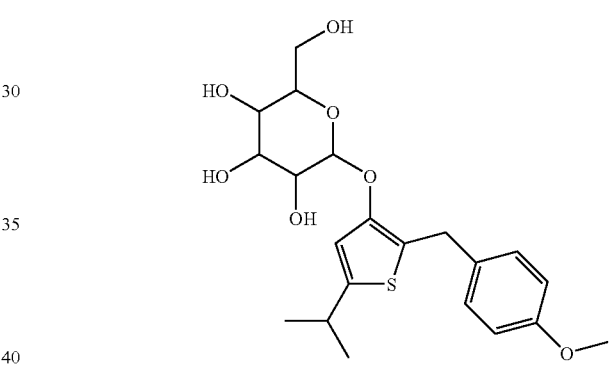

h) 2-Hydroxymethyl-6-[5-isopropyl-2-(4-methoxy-benzyl)-thiophen-3-yloxy]-tetrahydro-pyran-3,4,5-yl-triol 450 mg of (4,5-diacetoxy-6-acetoxymethyl-2-[5-isopropyl-2-(4-methoxy-benzyl)-thiophen-3-yloxy]-tetrahydro-pyran-3-yl) acetate were dissolved in 20 ml of methanol, and 0.41 of a 30% strength methanolic sodium mathanolate solution was added. The reaction mixture was stirred at 22° C. for 1 h and, after addition of Amberlyst 15 (H$^+$ form), filtered and washed with 30 ml of methanol. The solution was concentrated.

The product with the molecular weight of 424.5 ($C_{21}H_{28}O_7S$), MS (ESI): 447 (M+Na$^+$) was obtained.

Examples 52 to 54 below were prepared by the same synthetic route starting from 3-hydroxy-thiophene-2-carboxylic acids known from the literature [h. Fiesselmann, F. Thomas, Chem. Ber. 1956, 89, 1907-1913; M. D. Mullican et al., J. Med. Chem. 1991, 34, 2186-2194; G. M. Karp et al., Synthesis 2000, 1078-1080.]:

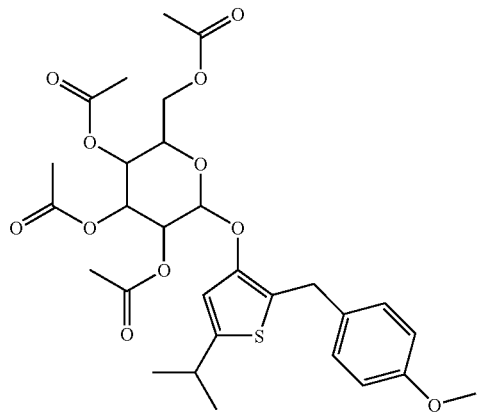

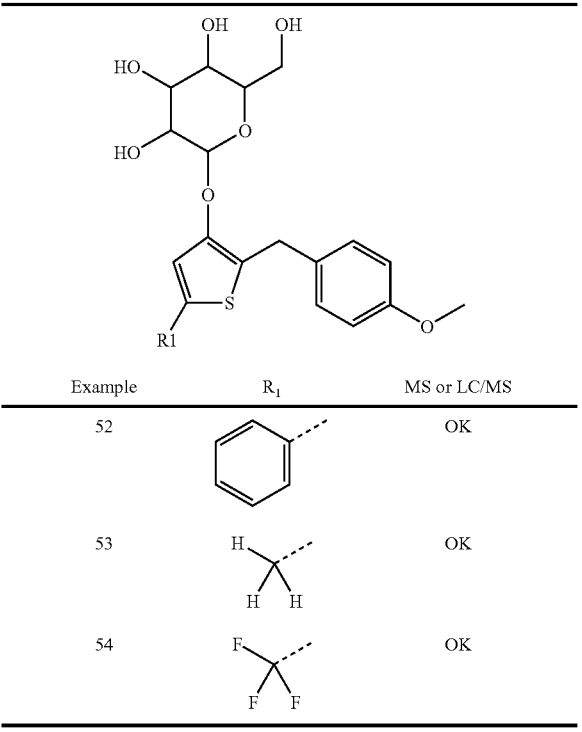

| Example | R₁ | MS or LC/MS |
|---|---|---|
| 52 | (phenyl) | OK |
| 53 | (CH₃) | OK |
| 54 | (CF₃) | OK |

Example 55

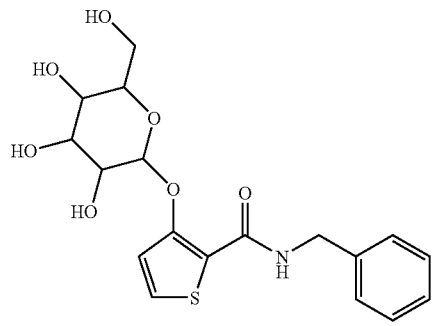

3-(3,4,5-Trihydroxy-6-hydroxymethyl-tetrahydro-pyran-2-yloxy)-N-benzylthiophene-2-carboxamide

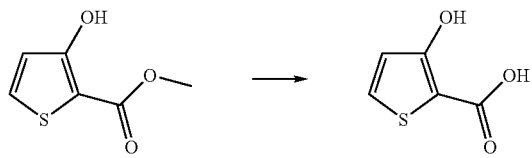

a) 3-Hydroxy-thiophene-2-carboxylic acid 10.0 g of methyl 3-hydroxy-thiophene-2-carboxylate were dissolved in a mixture of 90 ml of tetrahydrofuran (THF) and 90 ml of methanol, and a solution of 25.2 g of lithium hydroxide in 25 ml of water was added. The reaction mixture was stirred at 22° C. for 18 h and then heated at 55° C. for 6 h. The reaction mixture was concentrated to 50 ml in a rotary evaporator, acidified to pH=1 with 2 molar hydrochloric acid and extracted 3 times with 50 ml of t-butyl methyl ether each time. The combined organic phases were dried over magnesium sulfate and concentrated.

The product with the molecular weight of 144.2 ($C_5H_4O_3S$), MS (ESI): 145 (M+H$^+$) was obtained.

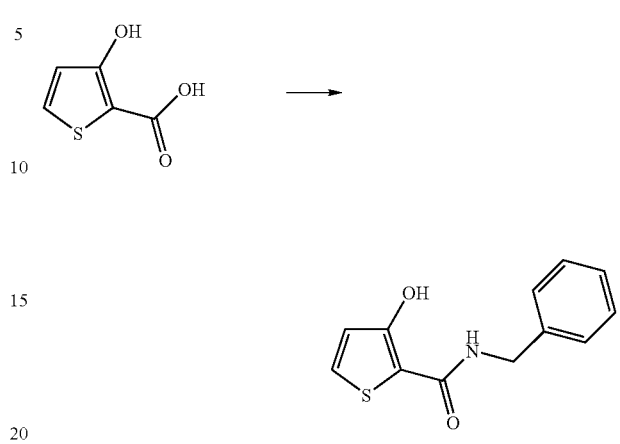

b) N-Benzyl-3-hydroxy-thiophene-2-carboxamide 1.44 g of 3-hydroxy-thiophene-2-carboxylic acid were dissolved in 100 ml of dichloromethane, and 2.18 ml of benzylamine and 5.00 ml of a 50% strength 1-propanephosphoric anhydride solution in acetic acid were added. The reaction mixture was stirred at 22° C. for 2 h and, after addition of 100 ml of saturated sodium bicarbonate solution, extracted twice with 100 ml of dichloromethane each time. The combined organic phases were washed with 100 ml of saturated sodium chloride solution, dried over magnesium sulfate and concentrated. The product with the molecular weight of 233.3 ($C_{12}H_{11}NO_2S$), MS (ESI): 234 (M+h$^+$) was obtained.

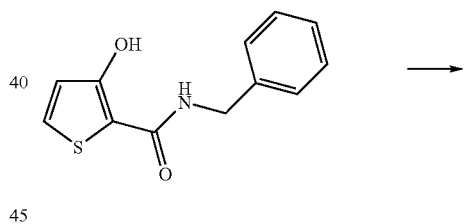

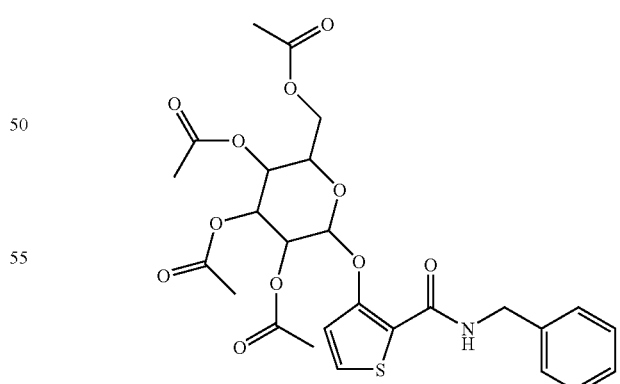

c) 3,4,5-Triacetoxy-6-(2-benzylcarbamoyl-thiophen-3-yloxy)-tetrahydro-pyran-2-ylmethyl acetate 1.12 g of N-benzyl-3-hydroxy-thiophene-2-carboxamide, 3.16 g of 4,5-diacetoxy-6-acetoxymethyl-2-bromo-tetrahydro-pyran-3-yl acetate, 3.30 g of potassium carbonate and 235 mg of benzyltributylammonium chloride were dissolved in 25 ml of dichloromethane, and 2.00 ml of water were added. The reaction mixture was stirred at 22° C. for 40 h. 50 ml of saturated sodium bicarbonate solution were added to the reaction mixture, which was extracted twice with 50 ml of dichloromethane each time. The combined organic phases were dried over magnesium sulfate and concentrated. The crude product was purified by column chromatography (SiO$_2$, ethyl acetate/n-heptane=1:1).

The product with the molecular weight of 563.6 (C$_{26}$H$_{29}$NO$_{11}$S), MS (ESI): 564 (M+H$^+$) was obtained.

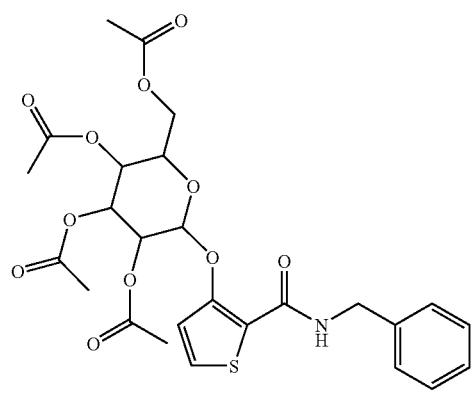

→

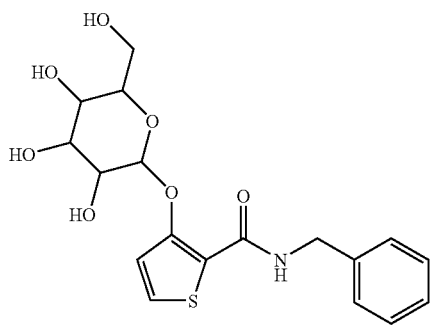

d) N-Benzyl-3-(3,4,5-trihydroxy-6-hydroxymethyl-tetrahydro-pyran-2-yloxy)-thiophene-2-carboxamide 600 mg of 3,4,5-triacetoxy-6-(2-benzylcarbamoyl-thiophen-3-yloxy)-tetrahydro-pyran-2-ylmethyl acetate were dissolved in 40 ml of methanol, and 1.40 ml of a 30% strength methanolic sodium methanolate solution were added. The reaction mixture was stirred at 22° C. for 2 h, neutralized with 0.5 molar methanolic HCl solution and concentrated. The crude product was purified by column chromatography (SiO$_2$, ethyl actate/methanol=10:1).

The product with the molecular weight of 395.4 (C$_{18}$H$_{21}$NO$_7$S), MS (ESI): 396 (M+H$^+$) was obtained.

Examples 56 to 58 below were prepared by the same synthetic route:

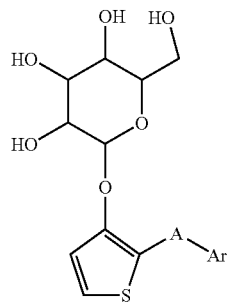

| Example | A | Ar | MS/LCMS |
|---|---|---|---|
| 56 | —CO—NH—CH$_2$— | 4-methoxyphenyl | OK |
| 57 | —CO—NH—CH$_2$— | benzo[1,3]dioxol-5-yl | OK |
| 58 | —CO—NH—CH$_2$— | 4-(trifluoromethoxy)phenyl | OK |

We claim:
1. A compound selected from the group:

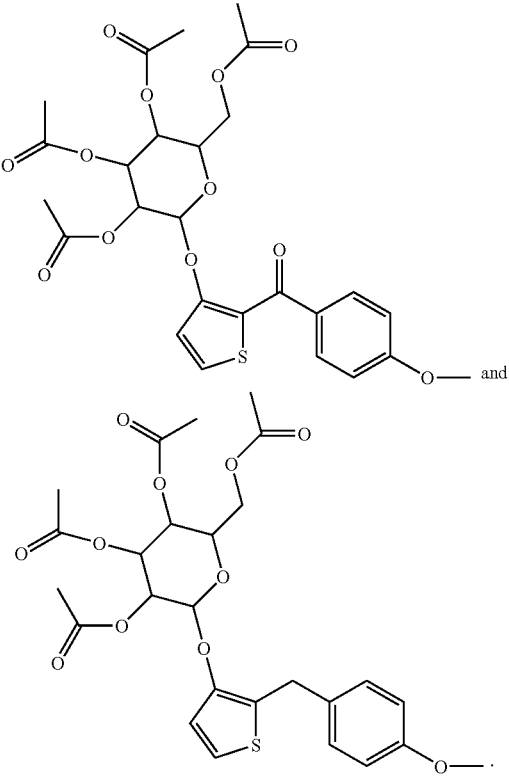

and

2. The compound of claim 1, wherein said compound is in its β-D-gluco form.

3. A pharmaceutical composition comprising at least one compound of the formula I

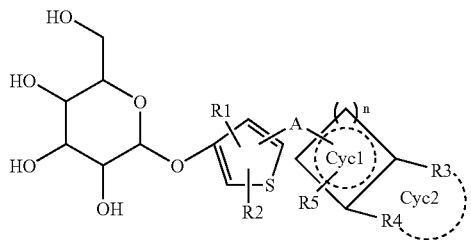

wherein
R1 is hydrogen, CF$_3$, (C$_1$-C$_4$)-alkyl, or phenyl;
R2 is hydrogen;
A is —CH=CH—CH$_2$— or (C$_1$-C$_4$)-alkanediyl,
  wherein one or two CH$_2$ groups are optionally replaced by —(C=O)—, —CH=CH—, —CH(OH)—, —NH—, —CHF—, —CF$_2$—, or —O—;
n is a number 2 or 3;
Cyc1 is unsaturated ring, wherein 1 carbon atom is optionally replaced by O or S;
R3, R4, R5 are, independently of each other, hydrogen, F, Cl, Br, I, OH, NO$_2$, ON, COOH, COO(C$_1$-C$_6$)-alkyl, CO(C$_1$-C$_4$)-alkyl, CONH$_2$, CONH(C$_1$-C$_6$)-alkyl, CON[(C$_1$-C$_6$)-alkyl]$_2$, (C$_1$-C$_8$)-alkyl, (C$_2$-C$_6$)-alkenyl, (C$_2$-C$_6$)-alkynyl, (C$_1$-C$_{12}$)-alkoxy, HO—(C$_1$-C$_6$)-alkyl, or (C$_1$-C$_6$)-alkoxy-(C$_1$-C$_6$)-alkyl,
  wherein one, more than one or all hydrogens in the alkyl and alkoxy radicals are optionally replaced by fluorine;
SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_o$-phenyl, SO—(C$_1$-C$_6$)-alkyl, SO—(CH$_2$)$_o$-phenyl, SO$_2$—(C$_1$-C$_6$)-alkyl, or SO$_2$—(CH$_2$)$_o$-phenyl,
  wherein o is 0-6 and wherein the phenyl radical is optionally substituted up to twice, each substituent chosen independently from F, Cl, Br, OH, CF$_3$, NO$_2$, CN, OCF$_3$, (C$_1$-C$_6$)-alkoxy, (C$_1$-C$_6$)-alkyl, and NH$_2$;
NH$_2$, NH—(C$_1$-C$_6$)-alkyl, N((C$_1$-C$_6$)-alkyl)$_2$, NH(C$_1$-C$_7$)-acyl, phenyl, (CH$_2$)$_o$-phenyl, O—(CH$_2$)$_o$-phenyl,
  wherein o is 0-6 and wherein the phenyl ring is optionally substituted one to 3 times, each substituent chosen independently from F, Cl, Br, I, OH, CF$_3$, NO$_2$, ON, OCF$_3$, (C$_1$-C$_8$)-alkoxy, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, and CONH$_2$;
or
R3 and R4 together with the carbon atoms carrying them are a 5- to 7-membered, saturated, partially or completely unsaturated ring Cyc2,
  wherein 1 or 2 carbon atoms in the ring are optionally replaced by N, O or S, and
  wherein Cyc2 is optionally substituted by (C$_1$-C$_6$)-alkyl, (C$_2$-C$_5$)-alkenyl, or (C$_2$-C$_5$)-alkynyl,
    wherein, in each substituent of Cyc2, one CH$_2$ group is optionally replaced by O, or substituted by H, F, Cl, OH, CF$_3$, NO$_2$, CN, COO(C$_1$-C$_4$)-alkyl, CONH$_2$, CONH(C$_1$-C$_4$)-alkyl, or OCF$_3$, and
R5 is hydrogen;

or a pharmaceutically acceptable salt thereof and a further active ingredient, selected from the group of biguanides or sulfonylureas.

4. The pharmaceutical composition of claim 3, wherein A is linked to the thienyl ring in position 2.

5. The pharmaceutical composition of claim 3 wherein
R3, R4, R5 are, independently of each other, hydrogen, F, Cl, Br, I, OH, NO$_2$, CN, COOH, COO(C$_1$-C$_6$)-alkyl, CO(C$_1$-C$_4$)-alkyl, CONH$_2$, CONH(C$_1$-C$_6$)-alkyl, CON[(C$_1$-C$_6$)-alkyl]$_2$, (C$_1$-C$_8$)-alkyl, (C$_2$-C$_6$)-alkenyl, (C$_2$-C$_6$)-alkynyl, (C$_1$-C$_{12}$)-alkoxy, HO—(C$_1$-C$_6$)-alkyl, (C$_1$-C$_6$)-alkoxy-(C$_1$-C$_6$)-alkyl, (C$_1$-C$_4$)-alkylphenyl, (C$_1$-C$_4$)-alkoxyphenyl, S—(C$_1$-C$_6$)-alkyl, or SO—(C$_1$-C$_6$)-alkyl,
  wherein one, more than one or all hydrogens in the alkyl or alkoxy radicals are optionally replaced by fluorine;
or
R3 and R4 together with the carbon atoms carrying them are a 5- to 7-membered, saturated, partially or completely unsaturated ring Cyc2,
  wherein 1 or 2 carbon atoms in the ring are optionally replaced by N, O or S, and
  wherein Cyc2 is optionally substituted by (C$_1$-C$_6$)-alkyl, (C$_2$-C$_5$)-alkenyl, or (C$_2$-C$_5$)-alkynyl,
    wherein in each substituent of Cyc2, one CH$_2$ group is optionally replaced by O, or substituted by H, F, Cl, OH, CF$_3$, NO$_2$, ON, COO(C$_1$-C$_4$)-alkyl, CONH$_2$, CONH(C$_1$-C$_4$)-alkyl, or OCF$_3$, and
R5 is hydrogen.

6. The pharmaceutical composition of claim 3, wherein
R3, R4, R5 are, independently of each other, hydrogen, F, Cl, Br, I, NO$_2$, OH, ON, (C$_1$-C$_6$)-alkyl, (C$_1$-C$_8$)-alkoxy, OCF$_3$, OCH$_2$CF$_3$, S(C$_1$-C$_4$)-alkyl, COOH, HO—(C$_1$-C$_4$)-alkyl, (C$_1$-C$_4$)-alkoxy-(C$_1$-C$_4$)-alkyl, (C$_1$-C$_2$)-alkylphenyl, or (C$_1$-C$_2$)-alkoxyphenyl, or
R3 and R4 together are —CH=CH—O—, —CH=CH—S—, —O—(CH$_2$)—O—, —O—CF$_2$—O—, or —CH=CH—CH=CH—, wherein p=1 or 2, and
R5 is hydrogen.

7. The pharmaceutical composition of claim 3 wherein
R1 is hydrogen, CF$_3$, (C$_1$-C$_4$)-alkyl, or phenyl,
R2 is hydrogen,
A is —CH$_2$—, —C$_2$H$_4$—, —C$_3$H$_6$—, —CH(OH)—, (C=O)—, —CH=CH—, —CH=CH—CH$_2$—, —CO—CH$_2$—CH$_2$— or —CO—NH—CH$_2$—;
n is a number 2 or 3;
Cyc1 is unsaturated ring, wherein 1 carbon atom is optionally replaced by S;
R3, R4, R5 are, independently of each other, hydrogen, F, Cl, I, NO$_2$, OH, CN, (C$_1$-C$_6$)-alkyl, (C$_1$-C$_8$)-alkoxy, O—CH$_2$-phenyl, OCF$_3$, S—CH$_3$, or COOH or
R3 and R4 together are —CH=CH—O—, —O—(CH$_2$)—O—, —O—CF$_2$—O—, —CH=CH—CH=CH—, wherein p=1 or 2, and
R5 is hydrogen.

8. The pharmaceutical composition of claim 3 wherein A is —CH$_2$— or —CH$_2$—CH$_2$—.

9. The pharmaceutical composition of claim 3 wherein Cyc1 is phenyl.

10. The pharmaceutical composition of claim 3 wherein Cyc1 is thienyl.

11. The pharmaceutical composition of claim 3 wherein Cyc1 is monosubstituted.

12. The pharmaceutical composition of claim 3 comprising a compound selected from the group consisting of:

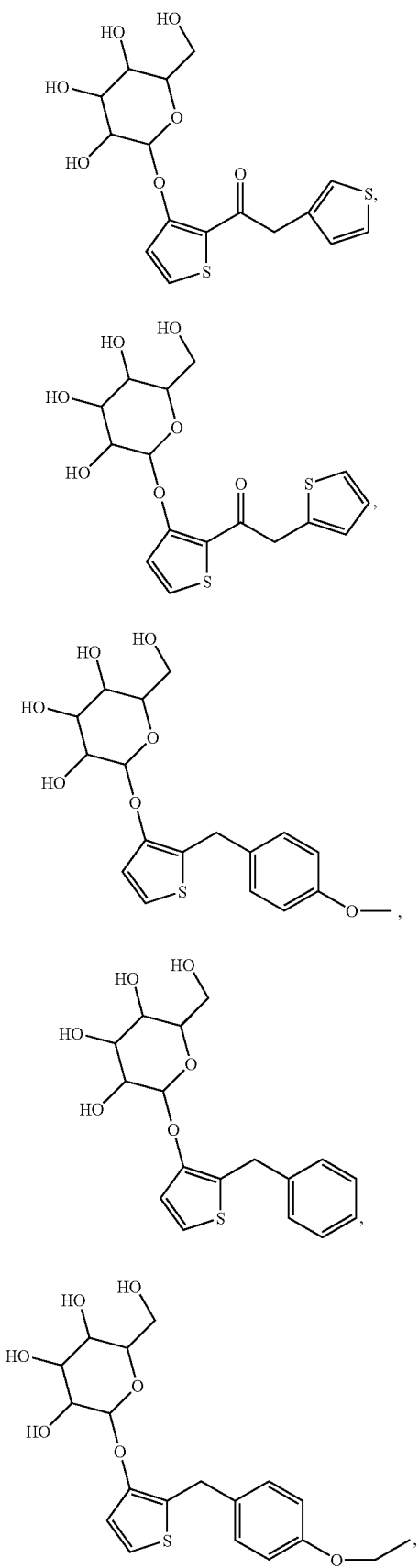
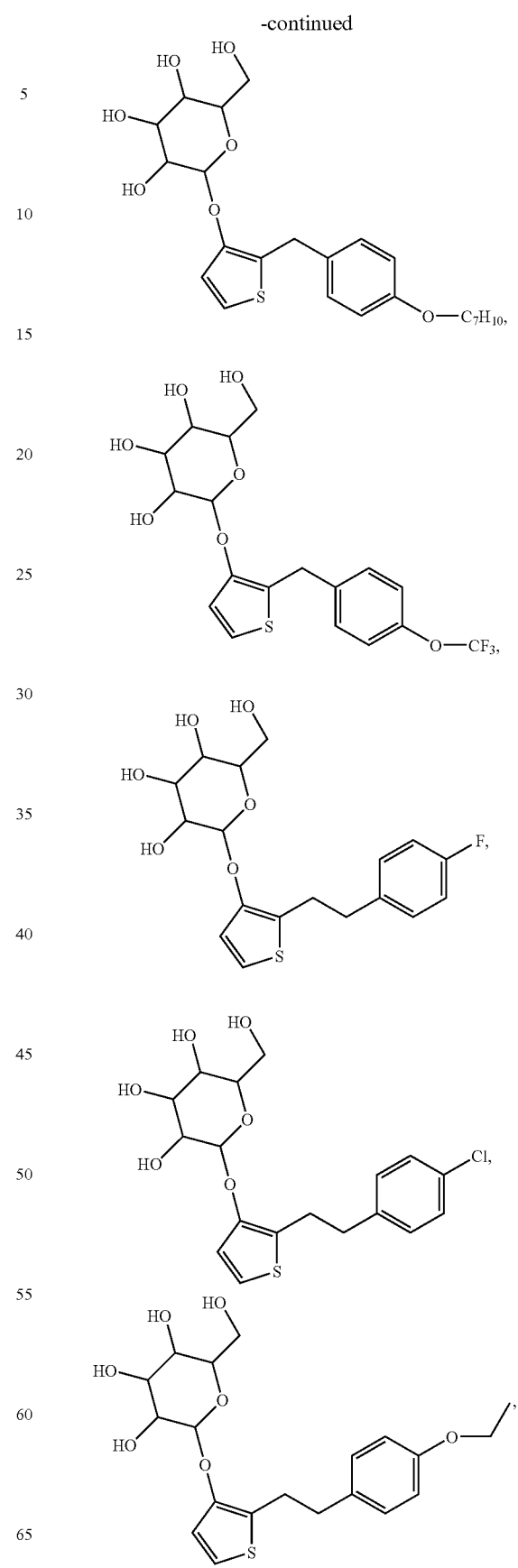

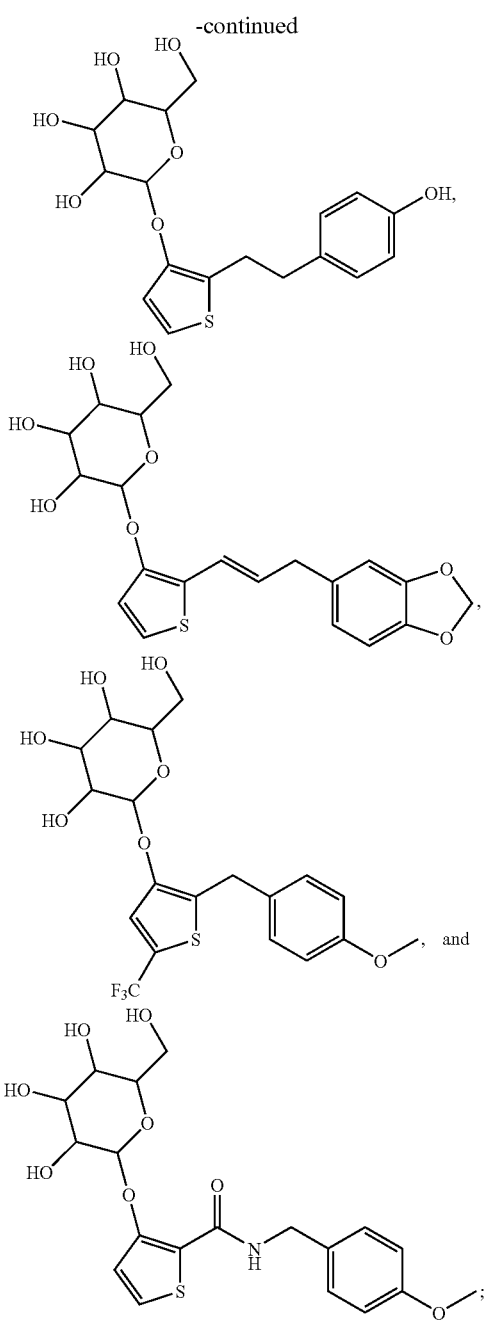

in its β-D-Gluco-form.

13. The pharmaceutical composition of claim 3 wherein the biguanide is Metformin.

14. The pharmaceutical composition of claim 3 wherein the Sulfonylurea is Tolbutamide, Glibenclamide, Glipizide or Glimepiride.

15. A method for treating type 1 or type 2 diabetes comprising administering to a patient with said conditions and in need of treatment thereof an effective amount of the pharmaceutical composition of claim 3.

16. A method for lowering blood glucose, comprising administering to a patient in need thereof an effective amount of the pharmaceutical composition of claim 3.

17. A method for treating type 1 or type 2 diabetes comprising administering to a patient with said conditions and in need of treatment thereof an effective amount of a compound of the formula I of claim 3 and Metformin.

18. A method for lowering blood glucose, comprising administering to a patient in need thereof an effective amount of a compound of the formula I of claim 3 and Metformin.

19. A method for treating type 1 or type 2 diabetes comprising administering to a patient with said conditions and in need of treatment thereof an effective amount of a compound of the formula I of claim 3 and a Sulfonylurea selected from the group Tolbutamid, Glibenclamid, Glipizid and Glimepirid.

20. A method for lowering blood glucose, comprising administering to a patient in need thereof an effective amount of a compound of the formula I of claim 3 and a Sulfonylurea selected from the group Tolbutamid, Glibenclamid, Glipizid and Glimepirid.

21. A method for treating type 1 or type 2 diabetes comprising administering to a patient with said conditions and in need of treatment thereof an effective amount of a compound of the formula I of claim 3 and insulin.

22. A method for lowering blood glucose, comprising administering to a patient in need thereof an effective amount of a compound of the formula I of claim 3 and insulin.

23. A method for treating late damage from diabetes such as nephropathy, retinopathy, neuropathy, syndrome X, obesitas, myocardial infarct, peripheral arterial occlusive diseases, thrombosis, arteriosclerosis, inflammations, immune diseases, and autoimmune dieseases, comprising administering to a patient with said conditions and in need of treatment thereof an effective amount of a compound of the formula I of claim 3.

24. The method of claim 23 wherein said late damage from diabetes is selected from nephropathy, retinopathy, neuropathy, syndrome X, obesitas, myocardial infarct and peripheral arterial occlusive diseases.

25. The method of claim 24 wherein said late damage from diabetes is selected from nephropathy, retinopathy, neuropathy, syndrome X and obesitas.

26. The method of claim 25 wherein said late damage from diabetes is selected from nephropathy, retinopathy and neuropathy.

* * * * *

UNITED STATES PATENT AND TRADEMARK OFFICE
CERTIFICATE OF CORRECTION

PATENT NO. : 7,666,848 B2 Page 1 of 1
APPLICATION NO. : 11/464338
DATED : February 23, 2010
INVENTOR(S) : Glombik et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 113 days.

Signed and Sealed this

Seventh Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,666,848 B2 | |
| APPLICATION NO. | : 11/464338 | |
| DATED | : February 23, 2010 | |
| INVENTOR(S) | : Glombik et al. | |

It is certified that error appears in the above-identified patent and that said Letters Patent is hereby corrected as shown below:

On the first page, in field (56), in column 2, under "Other Publications", line 7, delete "lontophoretic" and insert -- Iontophoretic --, therefor.

In column 1, line 41, delete "$(C_1-C_5)$" and insert -- $(C_1-C_6)$ --, therefor.

In column 1, line 64, after "–C≡C–," insert -- –S–, --.

In column 1, line 45, delete "alkynl," and insert -- alkynyl, --, therefor.

In column 2, line 64, delete "$(C_1-C_1)$-" and insert -- $(C_1-C_{12})$- --, therefor.

In column 4, line 12, delete "βglucose." and insert -- β-glucose. --, therefor.

In column 4, line 31, delete "teh" and insert -- the --, therefor.

In column 6, line 9, delete "an be" and insert -- can be --, therefor.

In column 6, line 67, delete "teh" and insert -- the --, therefor.

In column 9, line 9, delete "tetrahydorfuran" and insert -- tetrahydrofuran --, therefor.

In column 10, line 51, delete "suflide" and insert -- sulfide --, therefor.

In column 13, line 20, delete "dichoride" and insert -- dichloride --, therefor.

In column 13, line 20, delete "dichloromethan" and insert -- dichloromethane --, therefor.

In column 15, line 48, delete "methnaolate" and insert -- methanolate --, therefor.

Signed and Sealed this
Twenty-first Day of June, 2011

David J. Kappos
*Director of the United States Patent and Trademark Office*

CERTIFICATE OF CORRECTION (continued)
U.S. Pat. No. 7,666,848 B2

In column 17, line 52-53, delete "aformentioned" and insert -- aforementioned --, therefor.

In column 18, line 16-17, delete "trifluoracetic acid" and insert -- trifluoroacetic acid --, therefor.

In column 18, line 60, delete "Caromax® Caromax®" and insert -- Caromax®, Caromax® --, therefor.

In column 25, line 16, delete "IC25" and insert -- $IC_{25}$ --, therefor.

In column 28, line 17, delete "β-D" and insert -- α-D --, therefor.

In column 31, line 2, delete "actate," and insert -- acetate, --, therefor.

In column 31, line 58, delete "actetate." and insert -- acetate. --, therefor.

In column 33, line 32, delete "actate" and insert -- acetate --, therefor.

In column 38, line 36, delete "$(M+H^+)$" and insert -- $(M+H^+)$. --, therefor.

In column 38, line 59-60, delete "actate," and insert -- acetate, --, therefor.

In column 38, line 63, delete "extraced" and insert -- extracted --, therefor.

In column 39, line 19, delete "actate" and insert -- acetate --, therefor.

In column 39, line 23, delete "actate" and insert -- acetate --, therefor.

In column 39, line 62, delete "Tricyclohexyphosphine" and insert -- Tricyclohexylphosphine --, therefor.

In column 41, line 30, delete "$(C_{19}H_{24})_7S);$" and insert -- $(C_{19}H_{24}O_7S);$ --, therefor.

In column 43, line 65, delete "n-heptaine" and insert -- n-heptane --, therefor.

In column 46, line 28, delete "(SiO2," and insert -- $(SiO_2,$ --, therefor.

In column 48, line 52, delete "mathanolate" and insert -- methanolate --, therefor.

In column 50, line 35, delete "$(M+h^+)$" and insert -- $(M+H^+)$ --, therefor.

In column 51, line 62, delete "actate" and insert -- acetate --, therefor.

In column 53, line 30, in claim 3, delete "ON," and insert -- CN, --, therefor.

In column 53, line 51, in claim 3, delete "ON," and insert -- CN, --, therefor.
In column 54, line 25, in claim 5, delete "Cyc2,one" and insert -- Cyc2, one --, therefor.

In column 54, line 27, in claim 5, delete "ON," and insert -- CN, --, therefor.

In column 54, line 32, in claim 6, delete "ON," and insert -- CN, --, therefor.

In column 54, line 33, in claim 6, delete "S($C_1$-$C_4$)-alkyl," and insert -- S–($C_1$-$C_4$)-alkyl, --, therefor.

In column 54, line 38, in claim 6, delete "–O–($CH_2$)–O–," and insert -- –O–($CH_2$)$_p$–O–, --, therefor.

In column 54, line 45, in claim 7, delete "(C=O)–," and insert -- –(C=O)–, --, therefor.

In column 54, line 54, in claim 7, delete "($CH_2$)–O–," and insert -- ($CH_2$)$_p$–O–, --, therefor.

In column 58, line 40, in claim 23, delete "dieseases," and insert -- diseases, --, therefor.